United States Patent [19]

Wilhelm et al.

[11] Patent Number: 5,475,003
[45] Date of Patent: Dec. 12, 1995

[54] 8-PHENYLCYCLOPENTENOQUINOLINE AND 8-PHENYLCYCLOHEXENOQUINOLINE DERIVATIVES

[75] Inventors: Robert S. Wilhelm, Mountain View; Sabine Axt, San Jose, both of Calif.

[73] Assignee: Syntex (U.S.A.) Inc., Palo Alto, Calif.

[21] Appl. No.: 205,666

[22] Filed: Mar. 3, 1994

[51] Int. Cl.$^6$ ..................................... A61K 31/47
[52] U.S. Cl. .............. 514/290; 546/79; 546/101
[58] Field of Search .............. 514/290; 546/79, 546/101

[56] References Cited

U.S. PATENT DOCUMENTS

| | | | |
|---|---|---|---|
| 4,563,460 | 1/1986 | Kuhla et al. | 514/260 |
| 4,678,791 | 7/1987 | Napier et al. | 514/290 |
| 5,001,131 | 3/1991 | Crossley et al. | 514/290 |

FOREIGN PATENT DOCUMENTS

| | | |
|---|---|---|
| 2028314 | 4/1991 | Canada. |
| 0184437A2 | 6/1986 | European Pat. Off.. |
| 0304063A2 | 2/1989 | European Pat. Off.. |

OTHER PUBLICATIONS

Nicholson, et al., *Differential modulation of tissue function and therapeutic potential of selective inhibitors of cyclic nucleotide phosphodiesterase isoenzymes*, TiPS 12:19–27 (1991).

Beavo, et al., *Primary sequence of cyclic nucleotide phosphodiesterase isozymes and the design of selective inhibitors*, TiPS 11:150–155 (1990).

Livi, et al., *Cloning and Expression of cDNA for a Human Low–$K_m$, Rolipram–Sensitive Cyclic AMP Phosphodiesterase*, Mol. Cell. Biol. 10:2678–2686 (1990).

Hirshman, et al., *Elevated mononuclear leukocyte phosphodiesterase in allergic dogs with and without airway hyperresponsiveness*, J. Allergy Clin. Immunol. 79:46–53 (1987).

Holden et al., *Monocyte Localization of Elevated cAMP Phosphodiesterase Activity in Atopic Dermatitis*, J. Invest. Dermatol. 87:372–376 (1986).

Glaser, et al., *TVX 2706–a new phosphodiesterase inhibitor with anti–inflammatory action Biochemical characterization*, 15:341–348 (1984).

Alvarez, et al., *Regulation of Cyclic AMP Metabolism in Human Platelets*, Mol. Pharmacol. 20:302–309 (1981).

Thompson, et al., *Cyclic Adenosine 3':5'–Monophosphate Phosphodiesterase*, J. Biol. Chem. 251:4922–4929 (1976).

*Primary Examiner*—Donald G. Daus
*Attorney, Agent, or Firm*—Rohan Peries

[57] ABSTRACT

The disclosed derivatives of 8-phenylcyclopentenoquinolines and 8-phenylcyclohexenoquinolines are useful as anti-inflammatory agents, immunosuppressive agents, anti-allograft, rejection agents, anti-graft-vs-host disease agents, anti-allergic agents, bronchodilation agents, anti-autoimmune agents, and analgetic agents.

21 Claims, No Drawings

8-PHENYLCYCLOPENTENOQUINOLINE AND 8-PHENYLCYCLOHEXENOQUINOLINE DERIVATIVES

BACKGROUND OF THE INVENTION

1. Field of the Invention

This invention relates to derivatives of 8-phenylcyclopentenoquinolines and 8-phenylcyclohexenoquinolines, useful as selective inhibitors of phosphodiesterase type IV (PDE IV) enzyme.

Background Information

Cyclic 3', 5'-adenosine monophosphate (cAMP) modulates a variety of cellular and physiologic functions in mammals, such as cell division, endocrine function, and the immune response. The level of cAMP is controlled by a class of enzymes called phosphodiesterases, which enzymatically deactivate cAMP. There are five general types of phosphodiesterases, which are categorized according to their function and the type of cell from which they are isolated. For instance, high-affinity phosphodiesterase (PDE III) is isolated from human platelet cells and modulates platelet aggregation. Another type of phosphodiesterase (PDE IV) is found in various tissues but is the predominant form in human leukocytes; this enzyme modulates leukocyte activation and function associated with the immune response and inflammation. Both of these phosphodiesterases implement their control by modulating the cellular level of cAMP in their respective cells. Thus, inhibition of phosphodiesterases provides a method of modulating any cellular and bodily function that is controlled by cAMP.

Compounds that are nonspecific phosphodiesterase inhibitors are known, i.e., these compounds inhibit all or multiple types of phosphodiesterases. [See, Beavo, J. A. and D. H. Reifsyder, Trends in Pharm. Science, 11:150–155 (1990); and Nicholson, C. D., R. A. J. Challiss and M. Shahid, Trends in Pharm. Science, 12:19–27 (1991).]Since cAMP is involved in so many functions throughout the body, a nonspecific phosphodiesterase inhibitor has the potential to alter all of the functions modulated by cAMP. Therefore nonspecific phosphodiesterase inhibitors are of limited value because of potential undesired side-effects.

It has surprisingly been discovered that derivatives of certain 8-phenylcyclopentenoquinolines and 8-phenylcyclohexenoquinolines are potent selective inhibitors of phosphodiesterase type IV (PDE IV) enzyme. These compounds are well suited for use as a treatment for any disorder in which PDE IV function plays a role, such as where leukocyte activation or function is involved. In particular, these compounds are especially well suited for use as anti-inflammatory agents, immunosuppressive agents, anti-allograft rejection agents, anti-graft-vs-host disease agents, anti-allergic agents, bronchodilation agents, anti-autoimmune disease agents, and analgetic agents.

SUMMARY OF THE INVENTION

One aspect of the present invention relates to compounds represented by the Formula:

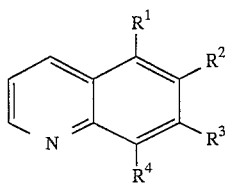

Formula I wherein:

$R^1$ and $R^2$ taken together represent —$CH_2$—$CH_2$—$CH_2$— or —$CH_2$—$CH_2$—$CH_2$—$CH_2$— and $R^3$ is hydrogen; or $R^2$ and $R^3$ taken together represent —$CH_2$—$CH_2$—$CH_2$— or —$CH_2$—$CH_2$—$CH_2$—$CH_2$— and $R^1$ is hydrogen; and $R^4$ is optionally substituted phenyl;

and the pharmaceutically acceptable salts or N-oxides thereof.

In another aspect, the invention relates to pharmaceutical compositions containing a therapeutically effective amount of a compound of Formula I or a pharmaceutically acceptable salt or N-oxide thereof admixed with at least one pharmaceutically acceptable excipient.

In still another aspect, the invention relates to a method of use of a compound of Formula I as anti-inflammatory agents, immunosuppressive agents, anti-allograft rejection agents, anti-graft-vs-host disease agents, anti-allergic agents, bronchodilation agents, anti-autoimmune disease agents, or analgetic agents, by administering to a mammal in need of such treatment a therapeutically effective amount of a compound of Formula I or a pharmaceutically acceptable salt or N-oxide thereof.

Yet another aspect of the invention relates to the treatment of the above conditions or diseases by the selective inhibition of PDE IV enzyme.

DETAILED DESCRIPTION

DEFINITIONS AND GENERAL PARAMETERS

The following definitions are set forth to illustrate and define the meaning and scope of the various terms used to describe the invention herein.

"Alkyl" means a monoradical branched or unbranched saturated hydrocarbon chain containing 1 to 12 carbon atoms, such as methyl, ethyl, propyl, tert-butyl, n-hexyl, n-octyl, n-decyl, and the like, unless otherwise indicated.

"Lower alkyl" means a monoradical branched or unbranched saturated hydrocarbon chain containing 1 to 6 carbon atoms, such as methyl, ethyl, propyl, isopropyl, tert-butyl, butyl, n-hexyl, and the like, unless otherwise indicated.

The term "lower alkoxy" refers to the group —O—R' where R' is lower alkyl.

The term "methylene" refers to the group —$CH_2$—.

The term "methylenedioxy" refers to the group —O—$CH_2$—O—.

The term "hydroxycarbonyl" refers to the group —C(O)OH.

The term "lower-alkoxycarbonyl" refers to the group —C(O)OR' where R' is lower-alkyl.

The term "carbamoyl" refers to the group —C(O)NR'R where R and R' are independently hydrogen or lower-alkyl, e.g., where R is hydrogen and R' is lower-alkyl the group is lower-alkylcarbamoyl, where R and R' are lower-alkyl the group is di-lower-alkylcarbamoyl.

The term "halo" refers to fluoro, bromo, chloro and iodo, unless otherwise indicated.

The term "lower-alkylthio" refers to the group R—S—, whereas R is lower-alkyl.

The term "lower-alkylsulfinyl" refers to the group R—S(O)—, whereas R is lower-alkyl.

The term "lower-alkylsulfonyl" refers to the group R—S(O)$_2$—, whereas R is lower-alkyl.

The term "lower-alkoxysulfonyl" refers to the group RO—S(O)—, whereas R is lower-alkyl.

The term "hydroxysulfonyl" refers to the group HO—S(O$_2$)—.

The term "optionally substituted phenyl" means that phenyl may or may not be substituted with a substituent selected from the group consisting of lower alkyl, lower alkoxy, hydroxy, nitro, trifluoromethyl, halo, thiol, amino, nitro, lower alkylthio, mono-lower-alkylamino, di-lower alkylamino, hydroxycarbonyl, lower alkoxycarbonyl, hydroxysulfonyl, lower alkoxysulfonyl, lower alkylsulfonyl, lower alkylsulfinyl, cyano, tetrazoyl, carbamoyl, lower alkylcarbamoyl, and di-lower alkylcarbamoyl, and encompasses all possible isomeric phenyl radicals that are mono, di or trisubstituted. Alternatively, the phenyl group may be substituted by methylenedioxy at two adjacent positions of the phenyl ring.

The term "aryl" refers to an aromatic monovalent carbocyclic radical having a single ring (phenyl) or two condensed rings (naphthyl), which can optionally be mono-, di-, or tri-substituted, independently, with hydrogen, hydroxyl, thiol, amino, halo, nitro, lower-alkylthio, lower-alkoxy, mono-lower-alkylamino, di-lower-alkylamino, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl.

The term "electron withdrawing group" refers to a radical group that has a greater affinity for electrons than a hydrogen atom would if it occupied the same position in the molecule. Typical electron withdrawing groups are halo (i.e., chloro, bromo, iodo and fluoro), nitro, trifluoromethyl, cyano, carboxy, methoxycarbonyl, methylcarbonyl (acetyl), and the like.

The term "leaving group" means a group capable of being displaced by a nucleophile in a chemical reaction, for example halo, alkyl sulfonates (e.g., methanesulfonate), aryl sulfonates, phosphates, sulfonic acid, sulfonic acid salts, and the like.

A "pharmaceutically acceptable salt" may be any salt derived from an inorganic or organic acid or base. Salts may be derived from acids or bases.

The acid addition salts are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, and the like.

The base addition salts are derived from inorganic bases such as sodium hydroxide, potassium hydroxide, lithium hydroxide, ammonia, calcium hydroxide, magnesium hydroxide and the like. Cations derived from organic bases include those formed from primary, secondary and tertiary amines, such as isopropylamine, diethylamine, trimethylamine, triethylamine, pyridine, cyclohexylamine, ethylene diamine, monoethanolamine, diethanolamine, triethanolamine, and the like.

As used herein, the term "allograft rejection" refers to the humoral or cellular immune response mounted by the immune system of a mammal after it has received a histoincompatible tissue graft from another mammal of the same species, thereby producing tissue injury to the graft in such a recipient.

As used herein, the term "graft-vs-host disease" refers to the immune response that originates from transplanted graft tissue, in particular, transplanted bone-marrow tissue, and that is directed towards the host tissue, thereby producing tissue injury in the host.

As used herein, the term "autoimmune disease" refers to disorders wherein the immune system of a mammal mounts a humoral or cellular immune response to the mammal's own tissue or to antigenic agents that are not intrinsically harmful to the mammal, thereby producing tissue injury in such a mammal. Examples of such disorders include, but are not limited to, systemic lupus erythematosus, rheumatoid arthritis, and Type I diabetes.

As used herein, the terms "treatment" or "treating" of a condition and/or a disease in a mammal, means:

(i) preventing the condition or disease, that is, avoiding any clinical symptoms of the disease;

(ii) inhibiting the condition or disease, that is, arresting the development or progression of clinical symptoms; and/or (iii) relieving the condition or disease, that is, causing the regression of clinical symptoms.

The conditions and diseases treated in the present invention include, inflammation, pain, pyrexia, autoimmune disease, allograft rejection, graft-vs-host, disease, allergies, and uveitis.

As used herein, the term "therapeutically effective amount" refers to that amount of a compound of Formula I which, when administered to a mammal in need thereof, is sufficient to effect treatment (as defined above) as an anti-inflammatory agent, immunosuppressive agent, anti-allograft rejection agent, anti-graft-vs-host disease agent, anti-allergy agent, autoimmune disease agent or analgetic agent. The amount that constitutes a "therapeutically effective amount" will vary depending on the compound, the condition or disease and its severity, and the mammal to be treated, but may be determined routinely by one of ordinary skill in the art with regard to contemporary knowledge and to this disclosure.

As used herein, the term "q.s." means adding a quantity sufficient to achieve a stated function, e.g., to bring a solution to a desired volume (e.g., 100 mL).

As used herein, the term "mp" refers to melting point. All temperatures are given in degrees Celsius (i.e. ° C.).

Unless specified to the contrary, the reactions described herein take place at atmospheric pressure. Unless specified to the contrary, the ranges of time and temperature described herein are approximate, e.g., "from 8 to 24 hours at 10° C. to 100° C." means from about 8 to about 24 hours at about 10° C. to about 100° C.

Isolation and purification of the compounds and intermediates described herein can be effected, if desired, by any suitable separation or purification procedure such as, for example, filtration, extraction, crystallization, column chromatography, preparative high pressure liquid chromatography (preparative HPLC), thin-layer chromatography or thick-layer chromatography, or a combination of these procedures. Specific illustrations of suitable separation and isolation procedures can be had by reference to the examples hereinbelow. However, other equivalent separation or isolation procedures can also be used.

The following numbering and nomenclature system will be used for naming the compounds of the invention.

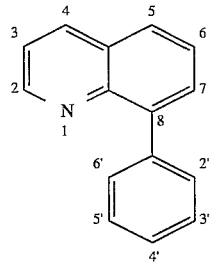

Some representative compounds are named in the following examples.

The compound represented by the formula:

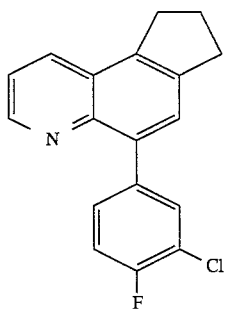

i.e., the compound of Formula I where $R^1$ and $R^2$ taken together represent —$CH_2$—$CH_2$—$CH_2$—, and $R^4$ is 3-chloro-4-fluorophenyl, is named:
8-(3'-chloro-4'-fluorophenyl)-5,6-cyclopentenoquinoline.

The compound represented by the formula:

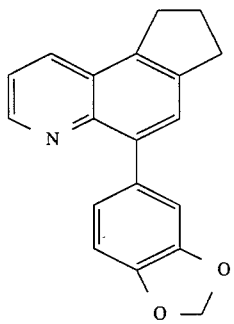

i.e., the compound of Formula I where $R^1$ and $R^2$ taken together represent —$CH_2$—$CH_2$—$CH_2$—, and $R^4$ is 3,4-methylenedioxyphenyl, is named:
5,6-cyclopenteno-8-(3', 4'-methylenedioxyphenyl) quinoline.

The compound represented by the formula:

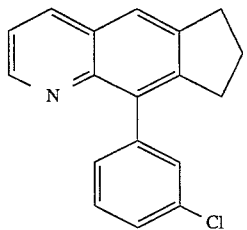

i.e., the compound of Formula I where $R^2$ and $R^3$ taken together represent —$CH_2$—$CH_2$—$CH_2$—, and $R^4$ is 3-chlorophenyl, is named:
8-(3'-chlorophenyl)-6,7-cyclopentenoquinoline.

The compound represented by the formula:

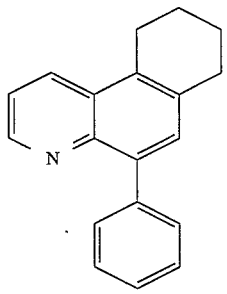

i.e., the compound of Formula I where $R^1$ and $R^2$ taken together represent —$CH_2$—$CH_2$—$CH_2$—$CH_2$—, and $R^4$ is phenyl, is named:
5,6-cyclohexeno-8-phenylquinoline.

The compound represented by the formula:

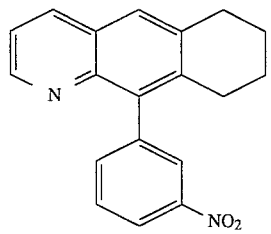

i.e., the compound of Formula I where $R^2$ and $R^3$ taken together represent —$CH_2$—$CH_2$—$CH_2$—$CH_2$—, and $R^4$ is 3-nitrophenyl, is named:
6,7-cyclohexeno-8-(3'-nitrophenyl)quinoline.

SYNTHESIS OF THE COMPOUNDS OF FORMULA I

As used in the Reaction Schemes, $R^1$, $R^2$, $R^3$, and $R^4$ are as defined in the Summary of the Invention unless otherwise indicated.

Reaction Scheme A illustrates the preparation of optionally substituted 5,6-cyclopenteno-8-phenylquinolines, i.e., the compounds of Formula I where $R^1$ and $R^2$ taken together represent —$CH_2$—$CH_2$—$CH_2$—.

Reaction Scheme B illustrates the preparation of optionally substituted 6,7-cyclopenteno-8-phenylquinolines, i.e., the compounds of Formula I, where $R^2$ and $R^3$ taken together represent —$CH_2$—$CH_2$—$CH_2$—.

Reaction Scheme C illustrates the preparation of optionally substituted 5,6-cyclohexeno-8-phenylquinolines and 8-phenyl-6,7-cyclohexenoquinolines, i.e., the compounds of Formula I, where $R^1$ and $R^2$ taken together represent —$CH_2$—$CH_2$—$CH_2$—$CH_2$—, or $R^2$ and $R^3$ taken together represent —$CH_2$—$CH_2$—$CH_2$—$CH_2$—, respectively.

STARTING MATERIALS

Referring to Reaction Schemes A, B and C, the compounds of Formula 1 (i.e., 5-aminoindan) and Formula 5 (i.e., 4-indanol) and Formula 10 (i.e., 7-nitrotetralone) are commercially available from Aldrich Chemicals Co., Inc. The compounds of Formula 4 (i.e., optionally substituted benzene boronic acid) are commercially available from Lancaster Synthesis Ltd., or alternatively can be prepared following the procedures described in Example 3 or in Organic Synthesis, Coll Vol 4. All the starting materials can be prepared by one of ordinary skill in art following procedures set forth in references such as, "Fieser and Fieser's Reagents for Organic Synthesis", Volumes 1–15, John Wiley and Sons, 1991; "Rodd's Chemistry of Carbon Compounds", Volumes 1–5 and Supplementals, Elsevier Science Publishers 1989; and "Organic Reactions" Volumes 1–40 John Wiley and Sons, 1991.

In the reaction schemes, compounds enclosed within square brackets (e.g., Reaction Scheme C, Preparation of Formulae 14 and 15) denote that both starting compounds (i.e., Formulae 12 and 13) are present and treated as a mixture.

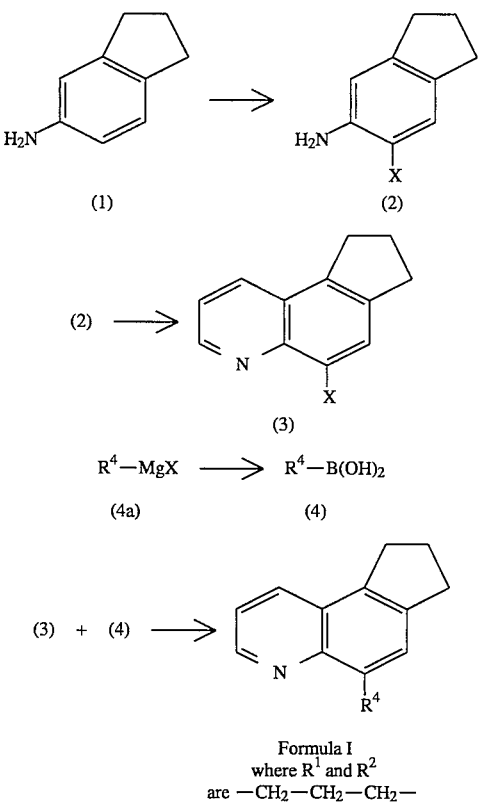

REACTION SCHEME A

Formula I
where $R^1$ and $R^2$
are —$CH_2$—$CH_2$—$CH_2$—

Preparation of Compounds of Formula 2

The starting material, 5-aminoindan (i.e., Formula 1) is dissolved in a polar anhydrous solvent, preferably dimethylformamide. To this solution is added about 1 to 2 molar equivalents of a halogenating reagent, preferably about 1 molar equivalent, such as N-bromosuccinimide, N-chlorosuccinimide or potassium iodide, preferably N-bromosuccinimide, preferably dissolved in the same solvent used for the starting material. The reaction mixture is stirred at a temperature of about 20°–30° C., preferably about room temperature, for a period of about ½ to 5 hours, preferably about 1½ hours. When the reaction is substantially complete, the compound of Formula 2 (where X is chloro, bromo or iodo) is isolated and purified by conventional means, preferably by flash column chromatography.

Preparation of Compounds of Formula 3

An aminohalobenzocyclopentene compound (Formula 2) is combined with about 2–4 mole equivalents of glycerol, preferably about 2.5 molar equivalents, and about ⅓ to 1 molar equivalents of arsenic pentoxide, preferably about 0.6 molar equivalents. The reaction mixture is heated to a temperature in the range of 80° to 110° C., preferably about 100° C., with stirring. About 1–3 molar equivalents of a concentrated acid, preferably concentrated $H_2SO_4$ is added in a gradual manner to the reaction mixture. The reaction mixture is heated to a temperature in the range of about 125°–170° C., preferably about 145°–150° C. under reflux conditions for a period of about 4–8 hours, preferably about 6 hours. The reaction mixture is then cooled to a temperature in the range of 60°–100° C., preferably about 80° C. Water (about 10 ml/mmol) is added to the reaction mixture followed by basification. When the reaction is substantially complete, the 5,6-cyclopenteno-8-haloquinoline of Formula 3 is isolated and purified by conventional means, preferably by flash column chromatography.

Preparation of Compounds of Formula 4

About 2 molar equivalents of trimethylborate is dissolved in an aprotic solvent (such as diethyl ether or tetrahydrofuran, preferably diethyl ether) and cooled to a temperature in the range of about –50° to –80° C., preferably about –65° C. An optionally substituted phenyl grignard reagent (Formula 4a where X is halo) is added to the solution in a gradual (e.g., dropwise) manner over a period of about 20 minutes/molar equivalent. The mixture is then stirred at a temperature in the range of about –50° C. to –80° C. for about 15 to 45 minutes, preferably about 30 minutes. The mixture is allowed to warm to about –10° C. to 10° C., preferably about 0° C. and stirred for a period of about 1 hour. When the reaction is substantially complete, the optionally substituted benzene boronic acid of Formula 4 is isolated and purified by conventional means, preferably by stirring in hexanes for a period of about 1 hour until a free flowing suspension forms. The suspension is filtered and air dried.

Preparation of Compounds of Formula I where $R^1$ and $R^2$ taken together represent —$CH_2$—$CH_2$—$CH_2$—

A 5,6-cyclopenteno-8-haloquinoline compound (Formula 3), an optionally substituted benzene boronic acid (Formula 4, about 1 molar equivalent), palladium tetrakis triphenylphosphine (about 0.1 molar equivalents), and an aqueous solution of a base, preferably 2M $Na_2CO_3$, (about 1–2 molar equivalents, preferably about 1 molar equivalent) are combined with a solvent or mixture of solvents, such as methanol, ethanol or benzene, preferably, a mixture of benzene and ethanol. The reaction mixture is refluxed for a period of about 1–3 hours, preferably about 2 hours, under an inert atmosphere. When the reaction is substantially complete, the 5,6-cyclopenteno-8-optionally substituted phenyl-quinoline of Formula I where $R^1$ and $R^2$ taken together represent —$CH_2$—$CH_2$—$CH_2$— is isolated and purified by conventional means, preferably by flash column chromatography.

REACTION SCHEME B

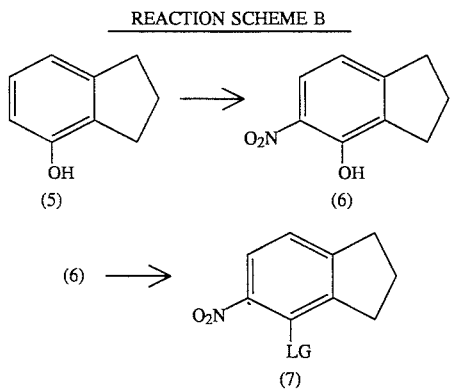

where LG is a leaving group.

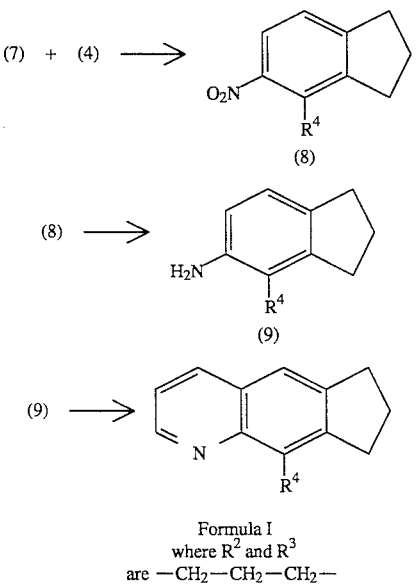

Formula I
where $R^2$ and $R^3$
are —$CH_2$—$CH_2$—$CH_2$—

Preparation of Compounds of Formula 6

The starting material, 4-indanol (i.e., Formula 5) is dissolved in an organic acid, preferably glacial acetic acid, at a temperature in the range of about 20°–30° C., preferably about room temperature. To this solution is added in a gradual manner a solution of concentrated nitric acid (about 1 to 2 molar equivalents, preferably about 1.5 molar equivalents) in an organic acid, preferably glacial acetic acid. The reaction mixture is stirred for a period of about 15 minutes to 1 hour, preferably about 30 minutes, at a temperature in the range of 20°–30° C., preferably about room temperature. When the reaction is substantially complete, the 4-hydroxy-5-nitrobenzocyclopentene of Formula 6 is isolated and purified by conventional means, preferably by flash column chromatography.

Preparation of Compounds of Formula 7

4-Hydroxy-5-nitrobenzocyclopentene (Formula 6) is dissolved in aprotic solvent, such as $CH_2Cl_2$, diethyl ether, THF, preferably $CH_2Cl_2$, and cooled to a temperature in the range of about −10° to 10° C., preferably about 0° C. To this solution is added a tertiary base, preferably triethylamine (about 4–6 molar equivalents, preferably about 5 molar equivalents), followed by the gradual addition of about 4–6 molar equivalents, preferably about 5 molar equivalents, of triflic anhydride. The reaction mixture was stirred at the same temperature for a period of about 10 to 30 minutes, preferably about 15 minutes. When the reaction is substantially complete, the O-derivatized 5-nitrobenzocyclopentene of Formula 7 (where LG is a leaving group) is isolated and purified by conventional means, preferably by flash column chromatography.

Preparation of Compounds of Formula 8

The O-derivatized nitrobenzocyclopentene compound (Formula 7), an optionally substituted benzene boronic acid (Formula 4) (about 1–3 molar equivalents, preferably about 2 molar equivalents), palladium tetrakis triphenylphosphine (about 0.05 molar equivalents) and 2M $Na_2CO_3$ (about 3–5 molar equivalents, preferably about 4 molar equivalents) are combined in a solvent or mixture of solvents, such as methanol, ethanol or benzene, preferably, a mixture of benzene and ethanol. The reaction mixture is refluxed for a period of about 30 minutes to 3 hours, preferably 1 hour, under an inert atmosphere. When the reaction is substantially complete, the phenylnitrobenzocyclopentene of Formula 8 is isolated and purified by conventional means, preferably by preparative TLC.

Preparation of Compounds of Formula 9

The phenylnitrobenzocyclopentene (Formula 8) is dissolved in a solvent, such as ethanol or methanol, preferably ethanol. To this solution is added 10% palladium on carbon (about 17 mg/mmol). The reaction mixture was hydrogenated for a period of about 12 to 24 hours, preferably about 18 hours. When the reaction is substantially complete, the phenylaminobenzocyclopentene of Formula 9 is isolated and purified by conventional means, preferably by preparative TLC. Preparation of Compounds of Formula I where $R^2$ and $R^3$ taken together represent —$CH_2$—$CH_2$—$CH_2$—

An optionally substituted phenylaminonitrobenzocyclopentene (Formula 9) is combined with glycerol (about 3–5 molar equivalents, preferably about 4 molar equivalents) and arsenic pentoxide (about ¼ to 1 molar equivalent, preferably about 0.6 molar equivalents) and heated to a temperature in the range of about 80° to 120° C., preferably about 100° C. About 3 molar equivalents of a strong acid (e.g., $H_2SO_4$) is added to the solution in a gradual manner with stirring. The reaction mixture is heated to a temperature in the range of about 145°–150° C. under reflux conditions for a period of about 1 to 3 hours, preferably about 2 hours. The reaction mixture is cooled to a temperature in the range of 60°–100° C., preferably about 80° C. Water (about 10 ml/mmol) is added to the reaction mixture followed by basification by the gradual addition of a base. When the reaction is substantially complete, the 5,6-cyclopenteno-8-phenylquinoline of Formula I (i.e. a compound of Formula I where $R^2$ and $R^3$ taken together represent —$CH_2$—$CH_2$—$CH_2$—) is isolated and purified by conventional means, preferably by preparative TLC.

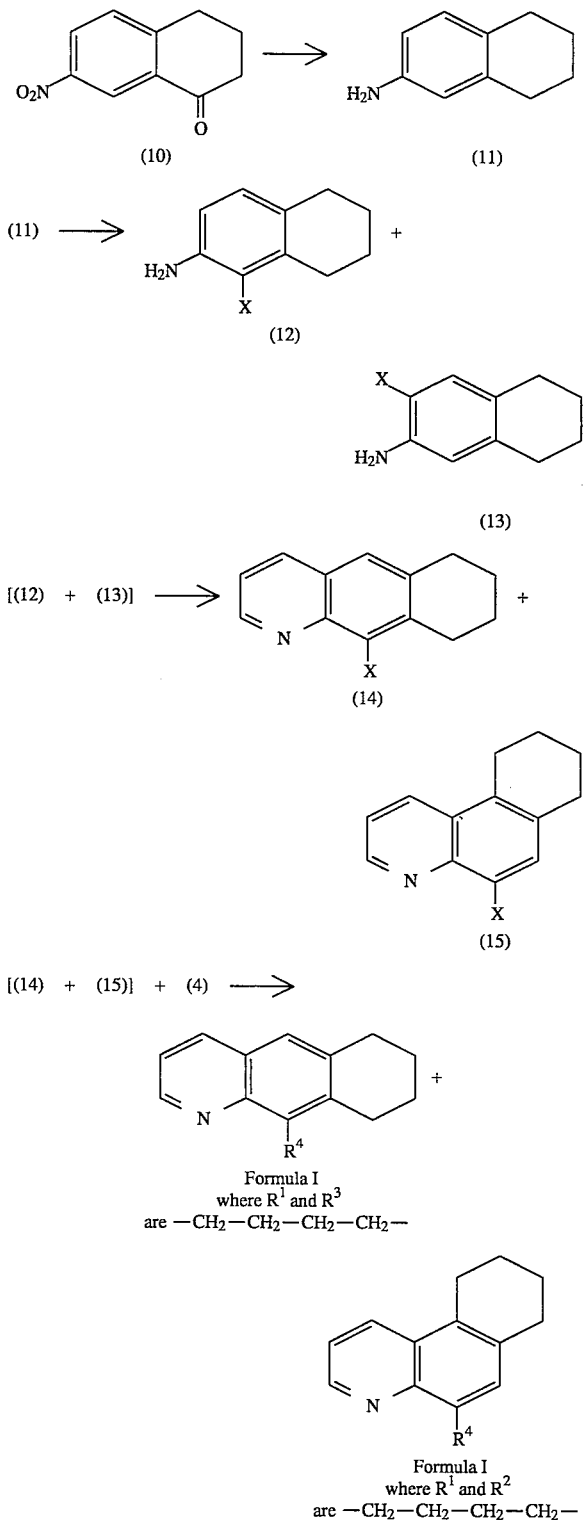

Preparation of a Compound of Formula 11

7-Nitrotetralone (Formula 10) is dissolved in a solvent, such as ethanol or methanol, preferably ethanol (about 4 L/mole). To this solution is added water (about 400 ml/mmol), concentrated HCl (about 95 ml/mmol) and 10% palladium on carbon (about 40 g/mmol). The reaction mixture is hydrogenated at a pressure of about 30–40 psi for a period of about 12 to 24 hours, preferably about 18 hours. When the reaction is substantially complete, 2-amino-5,6,7,8-tetrahydronaphthalene of Formula 11 is isolated and purified by conventional means, preferably by preparative TLC or flash column chromatography.

Preparation of Compounds of Formulae 12 and 13

2-Amino-5,6,7,8-tetrahydronaphthalene (Formula 11) is halogenated following procedures previously described (Reaction Scheme A, Preparation of Formula 2) yielding a mixture of two aminohalobenzocyclohexene isomers (i.e., compounds of Formula 12 and Formula 13).

Preparation of Compounds of Formula 14 and 15

A mixture of two aminohalobenzocyclohexene isomers (Formula 12 and Formula 13) are combined with glycerol (about 3–5 molar equivalents, preferably about 4 molar equivalents), $FeSO_4 \cdot 7H_2O$ (about 0.1 molar equivalents) and nitrobenzene (about 0.6 molar equivalents). The reaction mixture is heated to a temperature in the range of 80° to 120° C., preferably about 100° C. with stirring. Concentrated $H_2SO_4$ (about 3 to 5 molar equivalents, preferably about 4 molar equivalents) is added in a gradual manner. After completion of the addition, the reaction mixture is heated to a temperature in the range of 145° to 150° C. under reflux conditions. After a period of about 2 to 4 hours, preferably about 3 hours, the reaction mixture is cooled to a temperature in the range of about 70° to 90° C., preferably about 80° C. To the reaction mixture is added a saturated solution of $NaHCO_3$ (about 3.5 ml/mmole of starting material) and the pH is adjusted to about 8. The organic materials are extracted (e.g., ethyl acetate), dried over a drying agent, filtered and evaporated. The mixture of 6,7-cyclohexeno-8-haloquinoline and 5,6-cyclohexeno-8-haloquinoline (i.e., compounds of Formulae 14 and 15, respectively) is isolated and purified by conventional means, preferably by flash chromatography.

Preparation of Compounds of Formula 1

A mixture of 6,7-cyclohexeno-8-haloquinoline and 5,6-cyclohexeno-8-haloquinoline (Formulae 14 and 15, respectively) are combined with an optionally substituted benzene boronic acid (about 1–2 molar equivalents), palladium tetrakis triphenylphosphine (about 0.05 to 0.15 molar equivalents, preferably about 0.1 molar equivalents) and 2M aqueous $Na_2CO_3$ solution (about 3 to 5 molar equivalents, preferably about 4 molar equivalents) in a solvent or mixture of solvents (e.g., methanol and benzene). The reaction mixture is refluxed for a period of 3 to 6 hours, preferably about 4.5 hours under an inert atmosphere. When the reaction is substantially complete, the desired 6,7-cyclohexenoquinoline derivative and the 5,6-cyclohexenoquinoline derivative (i.e., compounds of Formula I where $R^2$ and $R^3$ taken together represent —$CH_2$—$CH_2$—$CH_2$—$C_2$—, or $R^1$ and $R^2$ taken together represent —$CH_2$—$CH_2$—$CH_2$—

CH$_2$—, respectively) are isolated and separated by conventional means, preferably by preparative TLC.

Preparation of Salts of Compounds of Formula I

The pharmaceutically acceptable salts of Formula I are prepared by dissolving a compound of Formula I in a suitable solvent (such as methanol, dioxane or diethyl ether) adding 1 to 3 molar equivalents (preferably about two molar equivalent) of an appropriate acid (such as hydrochloric acid gas) or base (such as an alkaline earth hydroxide, e.g., lithium hydroxide, calcium hydroxide, potassium hydroxide, sodium hydroxide or the like; preferably sodium hydroxide) and stirring. The salt is isolated conventionally, for example by lyophilization or by precipitation, using techniques that will be apparent to those skilled in the art.

PREFERRED COMPOUNDS

Among the family of compounds of the present invention, one preferred category includes the compounds where $R^4$ is phenyl or phenyl substituted by an electron withdrawing group, especially phenyl optionally substituted by methylenedioxy, halo, nitro, trifluoromethyl, or cyano. Within this category a preferred group includes the compounds where $R^1$ and $R^2$ taken together represent —CH$_2$—CH$_2$—CH$_2$—CH$_2$—. Within this group a preferred subgroup includes those compounds where $R^4$ is substituted at the 3-position by nitro or chloro.

A second preferred group includes the compounds where $R^1$ and $R^2$ taken together represent —CH$_2$—CH$_2$—CH$_2$—. Within this group a preferred subgroup includes those compounds where $R^4$ is substituted at the 3-position by nitro or chloro.

A third preferred group includes the compounds where $R^2$ and $R^3$ taken together represent —CH$_2$—CH$_2$—CH$_2$—CH$_2$—. Within this group a preferred subgroup includes those compounds where $R^4$ is substituted at the 3-position by nitro or chloro.

A fourth preferred group includes the compounds where $R^2$ and $R^3$ taken together represent —CH$_2$—CH$_2$—CH$_2$—. Within this group a preferred subgroup includes those compounds where $R^4$ is substituted at the 3-position by nitro or chloro.

At present the most preferred compounds are:
6,7-cyclohexeno-8-(3'-nitrophenyl)quinoline;
5,6-cyclohexeno-8-(3'-nitrophenyl)quinoline; and
5,6-cyclopenteno-8-(3'-nitrophenyl)quinoline.

PREFERRED PROCESSES AND LAST STEPS

A preferred process for making 8-optionally substituted-5,6-cyclopentenoquinolines involves combining the corresponding optionally substituted benzene boronic acid with the corresponding 8-bromo-5,6-cyclopentenoquinoline.

A preferred process for making 8-optionally substituted-phenyl-6,7-cyclopentenoquinolines involves combining the corresponding optionally substituted 5-amino-4-(optionally substituted phenyl)indan with glycerol and arsenic pentoxide.

A preferred process for making 8-optionally substituted-5,6-cyclohexenoquinolines and 8-optionally substituted-6,7-cyclohexenoquinolines involves combining the corresponding optionally substituted benzene boronic acid with a mixture of the corresponding 8-bromo-5,6-cyclohexenoquinolines and 8-bromo-6,7-cyclohexenoquinolines.

UTILITY, TESTING AND ADMINISTRATION

GENERAL UTILITY

The compounds of this invention, including the pharmaceutically acceptable salts and N-oxides thereof, and the compositions containing them are particularly useful as anti-inflammatory, immunosuppressive, anti-allograft rejection, anti-graft-vs-host disease, anti-allergic agents, bronchodilation agents, anti-autoimmune disease or analgetic agents. The compounds of this invention act as PDE IV selective inhibitors, thereby modulating cAMP levels. Thus, these compounds are of use for the treatment of cAMP related conditions or diseases, particularly those that are modulated by leukocyte cAMP.

For example, inflammation, autoimmune diseases, graft-vs-host disease and allograft rejection are conditions that are manifested by the proliferation of lymphocytes. The proliferation is triggered by the presence of cAMP at specific levels. Inhibition of lymphocyte proliferation is accomplished by increasing levels of cAMP resulting from the inhibition of lymphocyte phosphodiesterase.

TESTING

Potency and selectivity of compounds as inhibitors of PDE IV is determined by following, for example, the procedures described in Example 19, or modifications thereof.

The immunomodulatory and anti-inflammatory activity of the compounds of the invention can be determined by a variety of assays utilizing both in vitro and in vivo procedures.

Inhibition of the proliferation of lymphocytes in response to mitogenic stimulation is determined by the procedures described by Greaves, et al. ["Activation of human T and B lymphocytes by polyclonal mitogens," *Nature,* 248, 698–701 (1974)], or modifications thereof (see, Example 20).

Inhibition of lymphocyte activation in response to antigenic challenge is determined in vitro by inhibition of a cytolytic T-cell assay (CTL) as described by Wunderlich, et al., *Nature* (1970), Vol. 228, p. 62, or a modification thereof.

Immune modulation is determined by in vivo procedures utilizing the Jerne Hemolytic Plaque Assay, [jerne, et al., "The agar plaque technique for recognizing antibody producing cells," *Cell-bound Antibodies,* Amos, B. and Kaprowski, H. editors (Wistar Institute Press, Philadelphia) 1963, p. 109] or a modification thereof (see, Example 21).

Anti-inflammatory activity is determined by the Arachidonic Acid-Induced Mouse Ear Edema Assay [Young, et al., *J. Invest. Derm.,* 82:367–371 (1984) ](see, Example 22) .

Anti-inflammatory activity is also determined by the Adjuvant Arthritis assay [Pearson, C. M., *Proc. Soc. Exp. Biol. Med.,* 91:95–101 (1956) ], or modifications thereof (see Example 23).

Anti-autoimmune activity in treating autoimmune disease can be determined utilizing the survivability of MRL/1 pr mice described by Theofilopoulos, et al., *Advances in Immunology,* Vol 37, pages 269–390 (1985) on pages 274–276, or a modification thereof (see Example 24).

Analgetic activity is determined by the Phenylquinone-induced Mouse Writhing Assay [Hendershot, et al., *J. Pharmacol. Exp. Ther.,* 125:237–240 (1959) ](see Example 25).

ADMINISTRATION

The compounds of this invention are administered at a therapeutically effective dosage, i.e., that amount which, when administered to a mammal in need thereof, is sufficient to effect treatment, as described above (for example, to reduce or otherwise treat inflammation, pain and/or pyrexia in the mammal). Administration of the active compounds and salts described herein can be via any of the accepted modes of administration for agents that serve similar utilities.

The level of the drug in a formulation can vary within the full range employed by those skilled in the art, e.g., from about 0.01 percent weight (%w) to about 99.99%w of the drug based on the total formulation and about 0.01%w to 99.99%w excipient. Preferably the drug is present at a level of about 10%w to about 70%w.

Generally, an acceptable daily dose is of about 0.001 to 50 mg per kilogram body weight of the recipient per day, preferably about 0.05 to 25 mg per kilogram body weight per day, and most preferably about 0.01 to 10 mg per kilogram body weight per day. Thus, for administration to a 70 kg person, the dosage range would be about 0.07 mg to 3.5 g per day, preferably about 3.5mg to 1.75 g per day, and most preferably about 0.7 mg to 0.7 g per day depending upon the individuals and disease state being treated. Such use optimization is well within the ambit of those of ordinary skill in the art.

Administration can be via any accepted systemic or local route, for example, via parenteral, oral (particularly for infant formulations), intravenous, nasal, bronchial inhalation (i.e., aerosol formulation), transdermal or topical routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. The compositions will include a conventional pharmaceutical carrier or excipient and an active compound of Formula I and, in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "*Remington's Pharmaceutical Sciences*" by E. W. Martin.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with a compound of Formula I. The level of the drug in a formulation can vary within the full range employed by those skilled in the art, e.g., from about 0.01 percent weight (%w) to about 99.99%w of the drug based on the total formulation and about 0.01%w to 99.99%w excipient. Preferably, the formulation will be about 3.5 to 60% by weight of the pharmaceutically active compound, with the rest being suitable pharmaceutical excipients.

INTRAVENOUS ADMINISTRATION

Intravenous injection has proven to be an important route of administration for therapeutic agents. The compounds of the present invention can be administered via this route, for example, by dissolving the compound, ester, ether or salt in a suitable solvent (such as water or saline) or incorporation in a liposomal formulation followed, by dispersal into an acceptable infusion fluid. A typical daily dose of a compound of the invention can be administered by one infusion, or by a series of infusions spaced over periodic intervals.

ORAL ADMINISTRATION

Oral administration can be used to deliver the compound of Formula I using a convenient daily dosage regimen which can be adjusted according to the degree of affliction or for renal impairment, or to compensate for the toxic effects of other medications administered contemporaneously. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt/wt% and 99.99 wt/wt% of the compound of Formula I, but preferably such compositions will contain between 25 wt/wt% and about 80 wt/wt%.

Preferably the compositions will take the form of a capsule, pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, polyvinylpyrrolidone, gum acacia, gelatin, cellulose and derivatives thereof, and the like. For oral administration to infants, a liquid formulation (such as a syrup or suspension) is preferred.

AEROSOL ADMINISTRATION

Aerosol administration is an effective means for delivering a therapeutic agent directly to the respiratory tract. Some of the advantages of this method are: 1) it circumvents the effects of enzymatic degradation, poor absorption from the gastrointestinal tract, or loss of the therapeutic agent to the hepatic first-pass effect; 2) it administers therapeutic agents which would otherwise fail to reach their target sites in the respiratory tract due to their molecular size, charge or affinity to extra-pulmonary sites; 3) it provides for fast absorption into the body via the alveoli of the lungs; and 4) it avoids exposing other organ systems to the therapeutic agent, which is important where exposure might cause undesirable side effects. For these reasons, aerosol administration is particularly advantageous for treatment of asthma, local infections of the lung, and other diseases or disease conditions of the lung and respiratory tract.

There are three types of pharmaceutical inhalation devices, nebulizers inhalers, metered-dose inhalers (MDI) and dry powder inhalers (DPI). Nebulizer devices produce a stream of high velocity air that causes the therapeutic agent (which has been formulated in a liquid form) to spray as a mist which is carried into the patient's respiratory tract. MDIs typically have the formulation packaged with a compressed gas. Upon actuation, the device discharges a measure amount of therapeutic agent by compressed gas, thus affording a reliable method of administering a set amount of agent. Historically, MDIs have used chlorofluorocarbons (CFC) as the compressed gas to propel the therapeutic agent. In recent years, CFCs have been linked with the depletion of the earth's ozone layer. As a result of this, alternative propellants that are non-ozone threatening are being sought out as potential replacements for CFCs.

DPIs administer therapeutic agents in the form of a free flowing powder that can be dispersed in the patient's inspiratory air-stream during breathing by the device. In order to achieve a free flowing powder, the therapeutic agent is formulated with an excipient, such as lactose. A measured amount of the therapeutic is stored in a capsule form and is dispensed to with each actuation. Examples of DPIs being used are Spinhaler® (for the administration of disodium cromoglycate), Rotahaler® (for albuterol) and Turbuhaler® (for terbutaline sulfate). All of the above methods can be used for administering the present invention, particularly for the treatment of asthma and other similar or related respiratory tract disorders.

LIPOSOMAL FORMULATIONS

Pharmaceutical formulations based on liposomes have recently reached human clinical trials. Their benefits are believed related to favorable changes in tissue distribution and pharmacokinetic parameters that result from liposome entrapment of drugs, and may be applied to the compounds of the present invention by those skilled in the art.

The formulations can be designed to either target drug to disease sites [see: Lopez-Berestein et al., *J. Infect. Dis.*, 151:704–710 (1985); Gotfredsen et al., *Biochemical Pharmacology*, 32:3389–3396 (1983)]; or to the reticuloendothelial system [see Eppstein et al., *Int. J. Immunotherapy*, 2:115–126 (1986)], to increase duration of drug action [see: Gabizon et al., *Cancer Res.*, 42:4734 (1982); Eppstein et al., Delivery Systems for Peptide Drugs, Eds. S. S. Davis, L. Illum and E. Tomlinson, Plenum Pub. Corp., New York, pp. 277–283; C. A. Hunt, *Biochemica et Biophysica Acta.*, 719:450–463 (1982); and Senior et al., *Biochemica et Biophysica Acta.*, 839:1–8 (1985)], or to divert a drug away from organs that are particularly sensitive to its toxic effects [see: Weinstein et al., *Pharmac. Ther.*, 24:207–233 (1983); Olson et al., *Eur. J. Cancer Clin. Oncol.*, 18:167–176 (1982); and Gabzion et al., supra.].

Controlled release liposomal liquid pharmaceutical formulations for injection or oral administration are described in U.S. Pat. No. 4,016,100. Liposomal applications for oral drug delivery of a lyophilized liposome/peptide drug mixture filled into intestine capsules have also been suggested, see U.S. Pat. No. 4,348,384. The foregoing are incorporated herein by reference.

SUPPOSITORIES

For systemic administration via suppository, traditional binders and carriers include, for example, polyalkaline glycol or triglycerides [e.g., PEG 1000 (96%) and PEG 4000 (4%)]. Such suppositories may be formed from mixtures containing active ingredients in the range of from about 0.5 wt/wt% to about 10 wt/wt%; preferably from about 1 wt/wt% to about 2 wt/wt%.

LIQUIDS

Liquid pharmaceutically administrable compositions can, for example, be prepared by dissolving, dispersing, etc. an active compound (about 0.5% to about 20%), as described above, and optional pharmaceutical adjuvants in a carrier, such as, for example, water, saline, aqueous dextrose, glycerol, ethanol and the like, to thereby form a solution or suspension.

Actual methods of preparing such dosage forms are known, or will be apparent, to those skilled in this art; for example, see *Remington's Pharmaceutical Sciences*, Mack Publishing Company, Easton, Pa., 16th Ed., 1980. The composition to be administered will, in any event, contain a quantity of the active compound(s) in a pharmaceutically effective amount for relief of the particular condition being treated in accordance with the teachings of this invention.

EXAMPLES

The following examples are given to enable those skilled in the art to more clearly understand and to practice the present invention. They should not be considered as limiting the scope of the invention, but merely as being illustrative and representative thereof.

Example 1

Preparation of Compounds of Formula 2

A. Formula 2 where X is Bromo

5-Aminoindan (3.0 g, 22.5 mmol) was dissolved in 10 ml of anhydrous dimethylformamide. A solution of N-bromosuccinimide (4.0 g, 22.5 mmol) in 10 ml anhydrous dimethylformamide was added, and the reaction mixture was stirred at room temperature for 1.5 hours. The reaction mixture was partitioned between ethyl acetate and water, and the separated organic layer washed twice with $H_2O$, then with brine. Drying over $Na_2SO_4$ followed by filtration and evaporation of solvent gave a dark brown oil as the crude product. Purification by flash chromatography (50% EtOAc/hexane) provided 5-amino-6-bromoindan (3.26 g, 68% yield), a compound of Formula 2 where X is bromo, as a brown oil which crystallized into a brown solid.

Analytical data: mp 42°–44° C.; $^1$H NMR (300 MHz, $CDCl_3$) δ 7.25 (s, 1H), 6.67 (s, 1H), 3.92 (bs, 2H), 2.82-2.75 (m, 4H), 2.08-2.00 (m, 2H); $^{13}$C NMR (300 MHz, $CDCl_3$) δ 144.92; 142.04, 135.77, 127.88, 111.86, 107.11, 32.70, 31.94, 25.86; MS (CI—$NH_3$) m/z 211; Elem. analysis calcd. for $C_9H_{10}BrN$: C, 50.97; H, 4.75; N, 6.60; Found: C, 51.10; H, 4.70; N, 6.61.

B. Formula 2, varying X

Similarly, following the procedures of Example 1A above, but replacing N-bromosuccinimide with other halogenating agents, the following intermediates of Formula 2 are prepared:
5-amino-6-chloroindan;
5-amino-6-fluoroindan; and
5-amino-6-iodoindan.

Example 2

Preparation of Compounds of Formula 3

A. Formula 3 where X is Bromo

5-Amino-6-bromoindan (2.0 g, 9.4 mmol) was combined with glycerol (2.34 g, 25.5 mmol) and $As_2O_5$ (1.3 g, 5.6 mmol). The mixture was warmed to 100° C. with stirring and concentrated $H_2SO_4$ (1.0 ml, 18.8 mmol) was added dropwise to the reaction mixture. The mixture was heated to 145°–150° C. with a reflux condenser attached. After 6 hours, the reaction mixture was cooled to 80° C. 100 ml of water was added and the reaction mixture was carefully basified by dropwise addition with 20% KOH. Extraction with ethyl acetate followed by drying the combined extracts with $Na_2SO_4$, filtration, and evaporation of the solvent under reduced pressure yielded the desired crude product as a dark brown oil (2.18 g). Purification by flash chromatography (10% EtOAc/hexane) gave 8-bromo-5,6-cyclopentenoquinoline (1.33 g, 57% yield), a compound of Formula 3 where X is bromo, as a light brown solid.

Analytical data: m.p. 99.8°–101.6° C.; $^1H$ NMR (300 MHz, $CDCl_3$) δ 149.89, 144.36, 142.52, 139.92, 133.22, 130.38, 126.38, 122.59, 121.56, 33.39, 30.59, 24.63; MS m/z 347; Elem. analysis calcd. for $C_{12}H_{10}BrN$: C, 58.09; H, 4.06; N, 5.65. Found: C, 57.83; H, 4.07; N, 5.34.

B. Formula 3, varying X

Similarly, following the procedures of Example 2A above, but replacing 5-amino-6-bromoindan with other compounds of Formula 2, the following intermediates of Formula 3 are prepared:
8-chloro-5,6-cyclopentenoquinoline;
5,6-cyclopenteno-8-fluoroquinoline; and
5,6-cyclopenteno-8-iodoquinoline.

Example 3

Preparation of Compounds of Formula 4

A. Formula 4 where $R^4$ is 3-Chlorophenyl

A solution of trimethylborate in 200 mL of ethyl ether was cooled to –65° C. 3-Chlorobenzene magnesium chloride (0.8M, 60 mL), i.e., a grignard reagent, was added to the solution in a dropwise manner over 20 minutes. The mixture was kept in the temperature range of –60° C. to –70° C. and stirred. After 30 minutes, the mixture was allowed to warm to 0° C. and stirred for 1 hour. The mixture was quenched with $H_2O$ (25 mL) and stirred at room temperature for 1 hour. The solvent was removed and the remaining mass was extracted with ethyl ether (3×100 mL). The organic layers were combined and washed with $H_2O$ (2×50 mL), dilute HCl (2×100 mL), $H_2O$ (2×50 mL) and brine 1×50 mL). The organic layer was dried with $MgSO_4$ and concentrated, and 100 mL of hexanes was added, and the mixture stirred for 1 hour. The resultant white precipitate was filtered off and allowed to air dry, yielding 4.6 g of 3-chlorobenzene boronic acid, a compound of Formula 4 where $R^4$ is 3-chlorophenyl, as a white solid.

B. Formula 4, varying $R^4$

The following representative intermediates of Formula 4 are either available commercially, or may be prepared according to Example 3A above, replacing 3-chlorobenzene magnesium chloride with other compounds of Formula 4a:
3-nitrobenzene boronic acid;
3-chloro-4-fluorobenzene boronic acid;
4-chlorobenzene boronic acid;
benzene boronic acid;
3,4-dichlorobenzene boronic acid;
3-bromobenzene boronic acid;
3-trifluoromethylbenzene boronic acid;
4-trifluoromethylbenzene boronic acid;
4-bromobenzene boronic acid; and
3,4-methylenedioxybenzene boronic acid.

Example 4

Preparation of Compounds of Formula I

A. Formula I where $R^1$ and $R^2$ taken together represent —$CH_2$—$CH_2$—$CH_2$—, and $R^4$ is Phenyl 8-Bromo-5,6-cyclopentenoquinoline (0.2 g, 0.80 mmol), benzene boronic acid (0,208 g, 1.6 mmol), palladium tetrakis triphenylphosphine (0. 092 g, 0.08 mmol) and 2M $Na_2CO_3$ solution (1.6 ml, 3.2 mmol) were combined in a solution of 2 ml ethanol and 7 ml benzene. The biphasic mixture was refluxed for 2 hours under a $N_2$ atmosphere. The solvents were evaporated in vacuo and the residue was taken up in EtOAc/$H_2O$. After separation, the aqueous layer was extracted again with EtOAc. The combined organic layers were washed with $H_2O$ and brine, dried over $Na_2SO_4$, filtered and evaporated to give 0.33 g of a brown solid. Purification by preparative TLC (10% EtOAc/hexane) yielded 5,6-cyclopenteno-8-phenylquinoline as an off-white solid (0.13 g, 67% yield).

Analytical data: m.p. 115°–116° C., $^1H$ NMR (300 MHz, $CDCl_3$) δ 8.89 (dd, 1H, J=1.8, 4.1), 8.14 (dd, 1H, J=1.8, 8.3), 7.69-7.64 (m, 3H), 7.50-7.36 (m, 4H), 3.30-3.12 (m, 4H), 2.35-2.25 (m, 2H); $^{13}C$ NMR (300 MHz, $CDCl_3$) δ 148.99, 145.54, 141.36, 140.29, 139.46, 139.31, 132.71, 130.68, 127.96, 127.60, 127.11, 125.71, 120.72, 33.79, 30.95, 24.78. MS m/z 245; IR (KBr) $v_{max}$ 2976, 2932, 1597, 1585, 1574, 1495, 1441, 1331, 1062 cm$^{-1}$; Elem. analysis calcd. for $C_{18}H_{15}N$: C, 88.13, H, 6.16, N, 5.71. Found: C, 87.86; H, 6.38; N, 5.80.

B. Formula I where $R^1$ and $R^2$ taken together represent —$CH_2$—$CH_2$—$CH_2$—, varying $R^4$ By following the procedures described in Example 4A above, but substituting benzene boronic acid with:
1. 3-chlorobenzene boronic acid;
2. 3-chloro-4-fluorobenzene boronic acid;
3. 4-chlorobenzene boronic acid; and
4. 3-nitrobenzene boronic acid;
the following compounds of Formula I where $R^1$ and $R^2$ taken together represent —$CH_2$—$CH_2$—$CH_2$—were prepared:
1. 8- (3'-chlorophenyl) -5,6-cyclopentenoquinoline;

Analytical data: m.p. 102°–103° C., $^1H$ NMR (300 MHz, $CDCl_3$) δ 8.90 (dd, 1H, J=1.8, 4.2), 8.16 (dd, 1H, J=7.1, 1.7), 7.43-7.33 (m, 3H), 3.32-3.14 (m, 4H), 2.36-2.26 (m, 2H); $^{13}C$ NMR (300 MHz, $CDCl_3$) 6 149.14, 146.25, 142.03, 141.38, 139.99, 137.91, 133.74, 132.81, 130.67, 129.10, 128.96, 127.62, 127.15, 125.70, 120.98, 33.75, 30.96, 24.75. MS m/z 279; IR (KBr) $v_{max}$ 2909, 1589, 1562, 1500, 1477, 1462, 1437, 1425, 1396, 1379, 1365, 1336, 1159, 1095, 1078, 1035 cm$^{-1}$; Elem. analysis calcd. for $C_{18}H_{14}NCl$: C, 7.28, H, 5.04, N, 5.01. Found: C, 77.55; H, 5.07; N, 4.84;
2. 8-(3'-chlor6-4'-fluorophenyl)-5,6-cyclopentenoquinoline;

Analytical data: m.p. 129°–131 ° C., $^1H$ NMR (300 MHz, $CDCl_3$) δ 8.88 (dd, 1H, J=1.8, 4.2), 8.17 (dd, 1H, J=1.8, 8.3), 7.7 (dd, 1H, J=2.0, 7.4), 7.60 (s, 1H0, 7.54 (m, 1H), 7.41 (dd, 1H, J= 4.2, 8.3), 7.23 (t, 1H, J=9.0), 3.23 (m, 4H), 2.31 (m, 2H); $^{12}H$ NMR (300 MHz, $CDCl_3$) δ 159.11, 149.16, 145.22, 141.37, 140.10, 137.00, 132.84, 132.64, 130.50, 130.41, 127.50, 125.73, 120.96, 116.10, 115.82, 33.74, 30.94, 24.75. MS m/z 297, IR (KBr) $v_{max}$ 2966, 2907, 2845, 1593, 1576, 1498, 1466, 1442, 1404, 1363, 1263, 1228, 1059 cm$^{-1}$; Elem. analysis calcd. for $C_{18}H_{13}NClF$; C, 72.61; H, 4.40, N, 4.70. Found: C, 72.65; H, 4.39, N, 4.59;

3. 8-(4'-chlorophenyl)-5,6-cyclopentenoquinoline;

Analytical data: m.p. 97°–99° C., $^1$H NMR (300 MHz, CDCl$_3$) δ 8.88 (dd, 1H, J=1.8, 4.2), 8.15 (dd, 1H, J=1.8, 8.3), 7.63-7.59 (m, 3H), 7.46-7.42 (m, 2H0, 7.40 (dd, 1H, J=4.1, 8.3), 3.31-3.12 (m, 4H), 2.38 -2.28 (m, 2H); $^{13}$C NMR δ 149.08, 145.36, 141.39, 139.77, 138.65, 138.12, 133.15, 132.78, 131.96, 128.13, 127.42, 125.73, 120.87, 33.77, 30.95, 24.76; MS m/z 279; IR (KBr) 3447, 2951, 1591, 1574, 1493, 1466, 1398, 1363, 1103, 1087, 1035, 1012 cm$^{-1}$; Elem. analysis calcd. for $C_{18}H_{14}NCl$: C, 77.28; H, 5.04; N, 5.01. Found: C, 77.56; H, 5.02; N, 4.99; and 4. 5,6-cyclopenteno-8-(3'-nitrophenyl)quinoline;

Analytical data: m.p. 154°–155 ° C., $^1$H NMR (300 MHz, CDCl$_3$) δ 8.88 (dd, 1H, J=1.8, 4.2), 8.57 (t, 1H, J=2.0 Hz), 8.27-8.23 (m, 1H), 8.20 (dd, 1H, J-1.9, 8.4), 8.06-8.03 (m, 1H), 7.69 (s, 1H), 7.63 (t, 1H, J=8.0 Hz), 7.44 (dd, 1H, J=4.2, 8.4), 3.37-3.17 (m, 4H), 2.39-2.32 (m, 2H); $^{13}$C NMR (300 MHz, CDCl$_3$) δ 149.30, 148.05, 145.02, 141.80, 141.48, 140.80, 136.95, 136.64, 132.94, 128.65, 127.68, 125.74, 125.63, 121.94, 121.14, 33.71, 30.98, 24.72. HRMS exact mass calcd. for $C_{18}H_{14}N_2O_2$ 290.1055, found 290.1051. Elem. analysis calcd. for $C_{18}H_{14}N_2O_2$: C, 74.47; H, 4.86; N, 9.65. Found: C, 74.42; H, 4.72; N, 9.61.

C. Formula I where $R^1$ and $R^2$ taken together represent —CH$_2$—CH$_2$—CH$_2$—, varying $R^4$ By following the procedures described in Example 4A above, substituting benzene boronic acid with other compounds of Formula 4, there are obtained the following representative compounds of Formula I where $R^1$ and $R^2$ taken together represent —CH$_2$—CH$_2$—CH$_2$—:

5,6-cyclopenteno-8-(3', 4'-dichorophenyl)quinoline;
8-(3'-bromophenyl)-5,6-cyclopentenoquinoline;
5,6-cyclopenteno-8-(3'-trifluoromethylphenyl)quinoline;
5,6-cyclopenteno-8-(4'-trifluoromethylphenyl)quinoline; and
8-(4,-bromophenyl)-5,6-cyclopentenoquinoline.

Example 5

Preparation of Compounds of Formula I

A. Formula I where $R^1$ and $R^2$ taken together represent —CH$_2$—CH$_2$—C$_2$—, and $R^4$ is 3,4-Methylenedioxyphenyl 8-Bromo-5,6-cyclopentenoquinoline (496 mg, 2.0 mmol) in 13 ml anhydrous THF was cooled to –78° C. under a N$_2$ atmosphere, and Sec-BuLi (1.3M in cyclohexane, 1.6 ml, 2.1 mmol) added dropwise. After 10 minutes, a solution of ZnCl$_2$ (0.5M in THF, 4 ml, 2.0 mmol) was added. After several minutes the cooling bath was removed and the solution stirred, warming to room temperature for 1 hour. In a second flask, bromo-3,4-methylenedioxybenzene (0.26 ml, 2.2 mmol) and palladium tetrakis triphenylphosphine (116 mg, 0.1 mmol) were stirred in 2 ml of anhydrous THF under N$_2$ atmosphere. To this slurry the zincate solution was added via canula and the reaction refluxed for 5.5 hours. The solution was then poured into EtOAc/H$_2$. Phase separation was followed by extraction of the aqueous layer with EtOAc. The combined organic layers were washed with water and brine, dried over Na$_2$SO$_4$, filtered and evaporated to provide 5,6-cyclopenteno-8-(3,4-methylenedioxyphenyl)quinoline as a light brown semilsolid. Trituration with ether followed by recrystallization from methanol gave pure product as an off-white solid (287 mg, 50%): m.p. 132°–134° C., $^1$H NMR (300 MHz, CDCl$_3$) δ 8.89 (dd, 1H, J=1.8, 4.1), 8.14 (dd, 1H, J=1.8, 8.4), 7.61 (s, 1H), 7.37 (dd, 1H, J=4.1, 8.3), 7.21 (d, 1H, J=1.6), 7.10 (dd, 1H, J=1.7, 8.0), 6.93 (d, 1H, J=8.0), 6.00 (s, 2H), 3.29-3.24 (m, 2H), 3.17-3.12 (m, 2H), 3.34-2.25 (m, 2H); $^{13}$C NMR (300 MHz, CDCl$_3$) δ 148.92, 147.15, 146.88, 145.55, 141.33, 139.12, 139.00, 134.20, 132.73, 127.38, 125.73, 123.90, 120.71, 111.57, 108.11, 101.01, 33.78, 30.91, 24.76. MS m/z 289

Example 6

Preparation of the Compound of Formula 6

4-Indanol (10.0 g, 74.5 mmol) was dissolved in 50 ml of glacial acetic acid at room temperature, and a solution of concentrated nitric acid (50 ml, 111.8 mmol) in 50 ml of glacial acetic acid was added dropwise. The reaction mixture was stirred for 30 minutes at room temperature and then poured into 500 ml of ice water. The mixture was extracted twice with EtOAc, the combined organic phases washed with H$_2$O (3 x), dried over Na$_2$SO$_4$, filtered and evaporated to give 10.8 g of a dark brown oil. The oil was purified by flash column chromatography (25% EtOAc/hexane) yielding 5-nitro-4-indanol (3.60 g, 27% yield) as yellow crystals.

Analytical data: m.p. 56°–57° C. $^1$H NMR (300 MHz, CDCl$_3$) δ 10.72 (bs, 1H) 7.93 (d, 1H, J=8.6), 6.84 (d, 1H, J=8.6), 3.00-2.94 (m, 4H), 2.23-2.13 (m, 2H); $^{13}$C NMR (300 MHz, CDCl$_3$) δ 156.21, 151.69, 133.77, 124.03, 116.37, 34.03, 29.16, 24.89; MS m/z 179; Elem. analysis calcd. for $C_9H_9NO_3$: C, 60.33; H, 5.06, N, 7.82. Found: C, 60.41; H, 5.05; N, 7.86.

Example 7

Preparation of Compounds of Formula 7

A. Formula 7 where LG is Trifluoromethanesulfonyloxy

5-Nitro-4-indanol (4.0 g, 22.3 mmol) was dissolved in 400 ml of CH$_2$Cl$_2$ and cooled to 0° C. Triethylamine (15.5 ml, 111.6 mmol) was added, followed by dropwise addition of triflic anhydride (18.8 ml, 111.6 mmol). The reaction mixture was stirred at 0 ° C. for 15 minutes, then poured into excess of a saturated NaHCO$_3$ solution. The organic layer was separated, washed with water, dried over Na$_2$SO$_4$, filtered and evaporated to give 8.5 g of crude product as a brown oil. Purification of the crude product by flash column chromatography (25% EtOAc/hexane) gave 5-nitro-4-trifluoromethanesulfonyloxyindan (6.4 g, 92% yield) as a redbrown oil, which crystallized to a solid. Analytical data: m.p. 44°–46° C.; $^1$H NMR (300 MHz, CDCl$_3$) δ 7.93 (d, 1H, J=8.1), 7.35 (d, 1H, J=8.2), 3.15-3.05 (m, 4H), 2.28-2.18 (m, 2H); $^{13}$C NMR (300 MHz, CDCl$_3$) δ 154.76, 140.13, 137.62, 125.59, 124.78, 124.26, 120.53, 116.28, 112.02, 33.69, 20.76, 25.82; MS m/z 311. Elemental analysis calculated for $C_{10}H_8F_3NO_5S$: C, 38.56%; H, 2.59%, N, 4.50%. Found C, 38.93%; H, 2.62%; N, 4.49%.

Example 8

Preparation of Compounds of Formula 8

A. Formula 8 where $R^4$ is Phenyl

5-Nitro-4-trifluorosulfonyloxyindan (0.300 g, 0.96 mmol), benzene boronic acid (0.235 g, 1.93 mmol), palladium tetrakis triphenylphosphine (0.044 g, 0.04 mmol) and 2M aqueous sodium carbonate solution (2.0 ml, 3.84 mmol) were combined in 8 ml of ethanol/benzene (1:1 vol ratio). The reaction mixture was refluxed for 1 hour under a $N_2$ atmosphere. Following reflux, all the solvents were removed under reduced pressure and the remaining solid was taken up in EtOAc/$H_2O$. After separation, the aqueous layer was extracted again with EtOAc, and the combined organic layers were washed with $H_2O$ and brine, dried over $Na_2SO_4$, filtered and evaporated to give a dark brown oil as the crude product. Purification on preparative TLC (25% EtOAc/ hexane) yielded 5-nitro-4-phenylindan (0.202 g, 87.6%) as a yellow oil. Analytical data: $^1H$ NMR (300 MHz, CDCl$_3$) δ 7.73 (d, 1H, J= 8.1), 7.45-7.33 (m, 3H), 7.29 (d, 1H, J=8.2), 7.26-7.20 (m, 2H), 3.02 (m, 2H), 2.70 (m, 2H), 2.07 (m, 2H); $^{13}C$ NMR (300 MHz, CDCl$_3$) δ 149.71, 145.76, 136.66, 132.80, 128.53, 127.92, 127.77, 123.61, 122.75, 33.45, 32.59, 25.34. MW 239, HRMS found 239.0941.

B. Formula 8 where $R^4$ is 3-Chlorophenyl

By following the procedures described in Example 8A above, substituting benzene boronic acid with 3-chlorobenzene boronic acid, there was obtained the following compound:
4-(3'-chlorophenyl)-5-nitroindan;

Analytical data: m.p. 51°–53° C.; $^1H$ NMR (300 MHz, CDCl$_3$) δ 7.78 (d, 1H, J=8.2), 7.35-7.27 (m, 3H), 7.22 (m, 1H), 7.13-7.06 (m, 1H), 3.06-3.01 (m, 2H), 2.72-2.67 (m, 2H), 2.17-2.06 (m, 2H); $^{13}C$ NMR (300 MHz, CDCl$_3$) δ 150.15, 145.75, 138.60, 134.37, 131.48, 129.84, 128.03, 127.95, 126.21, 124.11, 123.01, 33.42, 32.52, 25.29. MW 273, HRMS found 273.0553.

C. Formula 8, varying $R^4$

By following the procedures described in Example 8A above, but substituting benzene boronic acid with other compounds of Formula 4, there are obtained the following representative compounds of Formula I:
5-nitro-4-(3'-nitrophenyl)indan;
5-nitro-4-(3'-chloro-4'-fluorophenyl)indan;
5-nitro-4-(4'-chlorophenyl)indan;
5-nitro-4-(3',4'-dichlorophenyl)indan;
5-nitro-4-(3'-bromophenyl)indan;
5-nitro-4-(3'-trifluoromethylphenyl)indan;
5-nitro-4-(4'-trifluoromethylphenyl)indan; and
5-nitro-4-(4'-bromophenyl)indan.

Example 9

Preparation of Compounds of Formula 9

A. Formula 9 where $R^4$ is Phenyl

5-Nitro-4-phenylindan (290 mg, 1.2 mmol) was dissolved in ethanol (5 ml) and 10% palladium on carbon (20 mg) added, and the reaction mixture was stirred under hydrogen at atmospheric pressure overnight. Filtration and evaporation of the solvent yielded a tan solid (210 mg) as crude product, which was purified by preparative TLC (25% EtOAc/hexane), yielding 5-amino-4-phenylindan as a light tan solid (152 mg, 60% yield). Analytical data: m.p. 73°–75° C.; $^1H$ NMR (300 MHz, CDCl$_3$) δ 7.46-7.40 (m, 2H), 7.35 - 7.29 (m, 3H), 7.02 (d, 1H, J=7.9 ), 6.61 (d, 1H, J=7.9), 3.3 (bs, 2H), 2.89-2.84 (m, 2H), 2.63-2.59 (m, 2H), 2.06-1.92 (m, 2H); $^{13}C$ NMR (300 MHz, CDCl$_3$) δ 143.87, 142.00, 138.11, 134.14, 129.58, 128.90, 128.86, 128.81, 127.19, 124.71, 123.96, 113.84, 113.79, 32.70, 32.61, 25.70. MW 209, HRMS found 209.1205.

B. Formula 9 where $R^4$ is 3-Chlorophenyl

Following the procedures described in Example 9A above, but substituting 5-nitro-4-phenylindan with 4-(3'-chlorophenyl)-5-nitroindan, 5-amino-4-(3'-chlorophenyl)indan was prepared.

Analytical data: m.p. 220°–222° C., $^1H$ NMR (300 MHz, CDCl$_3$) δ 7.42-7.20 (m, 6H), 2.98 (m, 2H), 2.68 (m, 2H), 2.05 (m, 2H); $^{13}C$ (300 MHz, CDCl$_3$) δ 175.84, 144.59, 134.65, 130.20, 129.84, 129.71, 128.95, 128.37, 128.05, 124.49, 124.08, 32.98, 32.43, 25.46. MW 243, HRMS found 243.0825.

C. Formula 9, varying $R^4$

By following the procedures described in Example 9A above, but substituting 5-nitro-4-phenylindan with other compounds of Formula 8, there are obtained the following representative compounds of Formula 9:
5-amino-4-(3-nitrophenyl)indan;
5-amino-4-(3-chloro-4'-fluorophenyl)indan;
5-amino-4-(4-chlorophenyl)indan;
5-amino-4-(3,4'-dichlorophenyl)indan;
5-amino-4-(3-bromophenyl)indan;
5-amino-4-(3-trifluoromethylphenyl)indan;
5-amino-4-(4-trifluoromethylphenyl)indan;
5-amino-4-(4-bromophenyl)indan; and
5-amino-4-(3,4'-methylenedioxyphenyl)indan.

Example 10

Preparation of Compounds of Formula I

A. Formula I where $R^2$ and $R^3$ taken together represent —CH$_2$—CH$_2$—CH$_2$—, and $R^4$ is Phenyl 5-Amino-4-phenylindan (150 mg, 0.96 mmol), glycerol (350 mg, 3.8 mmol) and arsenic pentoxide (132 mg, 0.57 mmol) were combined and warmed to 100° C. To the stirred mixture, concentrated $H_2SO_4$ (0.15 ml, 3.0 mmol) was added dropwise to the reaction mixture, followed by heating to 145°–150° C. for 2 hours. The reaction mixture was cooled to 80° C., and 10 ml of $H_2O$ added. The mixture was basified by dropwise addition of 10% aqueous KOH, followed by extraction with EtOAc (3 x), drying over $Na_2SO_4$, filtration, and evaporation of the solvent to yield the crude product as a brown oil (156 mg). Purification by preparative TLC (25% EtOAc/hexane) gave 6,7-cyclopenteno-8-phenylquinoline as a light brown oil (100 mg, 57% yield).

Analytical data: $^1H$ NMR (300 MHz, CDCl$_3$) δ 8.81 (dd, 1H, J= 1.9, 4.2), 8.09 (dd, 1H, J=1.8, 8.2), 7.64 (2, 1H), 7.52-7.36 (m, 5H), 7.30 (dd, 1H, J=4.2, 8.2), 3.16-3.12 (m, 2H), 2.96-2.91 (m, 2H), 2.17-2.05 (m, 2H); $^{13}C$ NMR (300 MHz, CDCl$_3$) δ 149.07, 143.84, 135.85, 130.36, 127.99, 127.88, 127.13, 121.32, 119.99, 33.15, 33.11, 26.20; MS m/z 245; HRMS calcd. for 245.1204, found 245.1197.

B. Formula I where $R^2$ and $R^3$ taken together represent —CH$_2$—CH$_2$—CH$_2$—, and $R^4$ is 3-Chlorophenyl Following the procedures described in Example 10A above, but substituting 5-amino-4-phenylindan with 4-(3'-chlorophenyl)-5-aminoindan, 8-(3'-chlorophenyl)-6,7-cyclopentenoquinoline was prepared.

Analytical data: m.p. 93°–95° C.; $^1$H NMR (300 MHz, CDCl$_3$) δ 8.80 (dd, 1H, J=1.8, 4.2), 8.09 (dd, 1H, J=1.8, 8.2), 7.64 (s, 1H), 7.44-7.32 (m, 4H), 7.30 (dd, 1H, J=4.1, 8.2), 3.16-3.11 (m, 2H), 2.96-2.91 (m, 2H), 2.17-2.07 (m, 2H); 13C NMR (300 MHz, CDCl$_3$) δ 149.34, 145.91, 143.77, 140.48, 135.65, 134.34, 133.80, 130.51, 129.21, 128.75, 127.83, 127.23, 121.79, 120.18, 33.074, 33.05, 26.21; MS m/z 279; Elem. analysis calcd. for C$_{18}$H$_{14}$ClN: C, 77.28; H, 5.04, N, 5.01. Found: C, 77.33; H, 5.09, N, 4.99.

Formula I where R$^2$ and R$^3$ taken together
represent —CH$_2$—CH$_2$—CH$_2$—, varying R$^4$ By following the procedures described in Example 10A above, but substituting 5-amino-4-phenylindan with other compounds of Formula 9, there are obtained the following representative compounds of Formula I where R$^2$ and R$^3$ taken together represent —CH$_2$—CH$_2$—CH$_2$—.

6,7-cyclopenteno-8-(3'-nitrophenyl)quinoline;
8-(3'-chloro-4'-fluorophenyl)-6,7-cyclopentenoquinoline;
8-(4'-chlorophenyl)-6,7-cyclopentenoquinoline;
6,7-cyclopenteno-8-(3', 4'-dichlorophenyl)quinoline;
8-(3'-bromophenyl)-6,7-cyclopentenoquinoline;
6,7-cyclopenteno-8-(3'-trifluoromethylphenyl)quinoline;
6,7-cyclopenteno-8-(4'-trifluoromethylphenyl)quinoline;
8-(4'-bromophenyl)-6,7-cyclopentenoquinoline; and
6,7-cyclopenteno-8-(3', 4'-methylenedioxyphenyl)quinoline.

Example 11

Preparation of the Compound of Formula 11

7-Nitrotetralone (20.0 g, 0.105 mmol) was dissolved in 400 ml of ethanol, and 40 ml of water, 10 ml of concentrated HCl, and 4.0 g of 10% palladium on carbon were added. The reaction mixture was reacted with hydrogen at 30–40 psi for 16 hours. Following hydrogenation, the reaction mixture was filtered and the solvents were evaporated, yielding white crystals. The crystals were washed with acetone, dissolved in cold 10% NaOH, and extracted with EtOAc (3 x). The combined organic layers were washed with water, dried over Na$_2$SO$_4$, filtered and evaporated, to give 2-amino-5,6,7,8-tetrahydronaphthalene (13.4 g, 87.1% yield) as a brown oil.

Analytical data: $^1$H NMR (300 MHz, CDCl$_3$) δ 6.86 (d, 1H, J= 8.0), 6.47 (dd, 1H, J=2.4, 7.9), 6.42 (d, 1H, J=2.4), 3.47 (bs, 2H), 2.67-2.65 (m, 4H), 1.77-1.73 (m, 4H); $^{13}$C NMR (300 MHz, CDCl$_3$) δ 143.87, 137.85, 129.82, 127.23, 115.41, 113.14, 29.49, 28.55, 23.53, 23.31; MS m/z 147; Elem. analysis calcd. for C$_{10}$H$_{13}$N: C, 81.58; H, 8.90; N, 9.51. Found: C, 81.28; H, 8.81; N, 9.21.

Example 12

Preparation of Compounds of Formulae 12 and 13

A. Formulae 12 and 13 where X is bromo

2-Amino-5,6,7,8-tetrahydronaphthalene (12.0 g, 81.5 mmol) was dissolved in 20 ml of dimethylformamide. A solution of N-bromosuccinimide (14.5 g, 81.5 mmol) in 30 ml of dimethylformamide was slowly added with stirring. Thirty minutes after completion of the addition, the solution was poured into 300 ml of water and brine added. The aqueous layer was extracted with 100 ml EtOAc (3 x), and the combined organic layers washed with H$_2$O (3 x) and brine. After drying over Na$_2$SO$_4$, filtration and evaporation, 18.1 g of crude product was obtained as a brown oil. Purification of the crude product by flash column chromatography (15% EtOAc/hexane) gave a brown oil consisting of a mixture of 2-amino-1-bromo-tetrahydronaphthalene and 2-amino-3-bromo-5,6,7,8-tetrahydronaphthalene in a ratio of 5 to 1 (14.3 g, 77.6% yield). The mixture of the two isomers was taken to the next step without further purification or isolation of the separate isomers.

Analytical data: $^1$H NMR (300 MHz, CDCl$_3$) δ 7.11 (s, 0.2H), 6.84 (d, 1H, J=8.0), 6.58 (d, 1H, J=7.9), 6.49 (s, 0.2H), 3.98 (bs, 2H), 3.86 (bs, 0.4H), 2.73-2.62 (m, 4.8H), 1.84-1.66 (m, 4.8H); $^{13}$C NMR (300 MHz, CDCl$_3$) δ 141.85, 136.79, 136.76, 132.44, 128.66, 128.77, 128.54, 115.94, 113.16, 112.78, 30.72, 29.36, 29.04, 28.25, 23.47, 23.24, 23.07, 22.82. MS m/z 225; Elem. analysis calcd. for C$_{10}$H$_{12}$NBr: C, 53.12; H, 5.35; N, 6.19. Found: C, 53.02, H, 5.34, N, 6.19.

Example 13

Preparation of Compounds Of Formulae 14 and 15

A. Formulae 14 and 15 Where X is Bromo

The mixture of 2-amino-1-bromo and 2-amino-3-bromo-5,6,7,8-tetrahydronaphthalene isomers (4.6 g, 20.3 mmol), prepared for example as shown in Example 12, was combined with glycerol (7.5 g, 81.4 mmol), FeSO$_4$•7H$_2$O (0.73 g, 2.6 mmol) and nitrobenzene (1.3 ml, 13.0 mmol) and warmed to 100 ° C. with stirring. Concentrated H$_2$SO$_4$ (4.3 ml, 81.4 mmol) was added dropwise to the reaction mixture with stirring. After completion of the addition, the reaction mixture was warmed to 145°–150° C. After 3 hours, the reaction mixture was cooled to approximately 80° C. Saturated NaHCO$_3$ (approximately 70 ml) was added to the reaction mixture, and the pH adjusted to 8 by the addition of 10% aqueous NaOH. The aqueous layer was extracted with EtOAc (3 x), and the combined organic layers washed with H$_2$O (3 x) and brine. After drying over Na$_2$SO$_4$, evaporation of the solvent gave 7.1 g of crude product as a dark brown oil. Flash column chromatography (25% EtOAc/hexane) yielded a brown oil consisting of 8-bromo-6,7-cyclohexenoquinoline and 8-bromo-5,6-cyclohexenoquinoline in a ratio of 5 to 1 (4.3 g, 80.0% yield). The mixture of the two isomers was taken to the next step without further purification or isolation of the separate isomers.

Analytical data: $^1$H NMR (300 MHz, CDCl$_3$) δ 8.97 (d, 0.2H, J= 1.5), 8.94 (dd, 1H, J=1.6, 4.2), 8.26 (dd, 0.2H, J=1.7, 8.7), 8.00 (dd, 1H, J=1.7, 8.3), 7.77 (s, 0.2H), 7.46 (s, 1H), 7.43 (dd, 0.2H, J=4.3, 8.6), 7.34 (dd, 1H, J=4.2, 8.6), 7.34 (dd, 1H, J=4.2, 8.2), 3.09-2.85 (m, 4.8H), 1.97-1.78 (m, 4.8H); $^{13}$C NMR (300 MHz, CDCl$_3$) δ 150.24, 149.62, 144.17, 144.10, 140.07, 138.21, 136.18, 135.62, 135.14, 131.98, 131.67, 128.84, 127.39, 126.54, 126.09, 121.72, 121.40, 121.06, 31.83, 30.55, 29.91, 25.11, 23.23, 22.56; MS m/z 261; Elem. analysis calcd. for C$_{13}$H$_{12}$H$_{12}$BrN: C, 59.56; H, 4.61; N, 5.34. Found: C, 59.76; H, 4.86, N, 5.24.

Example 14

Preparation of Compounds of Formula I

A. Formula I where R$^1$ and R$^2$ taken together and R$^2$ and R$^3$ taken together represent —CH$_2$—CH$_2$—CH$_2$—CH$_2$—, and R$^4$ is Phenyl A mixture of 8-bromo-6,7-cyclohexenoquinoline and 8-bromo-5,6-cyclhexenoquinoline in a ratio of 5 to 1 (400 mg, 1.5 mmol), prepared for example as shown in Example 13, was combined with benzene boronic acid (372 mg, 3.0 mmol), palladium tetrakis triphenylphosphine (176 mg, 0.15 mmol) and 2M aqueous $Na_2CO_3$ solution (3.0 ml, 6.0 mmol) in a solution of 3 ml methanol and 10 ml benzene. The biphasic mixture was refluxed for 4.5 hours under a $N_2$ atmosphere. The solvents were evaporated, the residue dissolved in EtOAc and washed with $H_2O$. The aqueous layer was extracted with EtOAc and the combined organic layers were washed with $H_2O$, brine, dried over $Na_2SO_4$, filtered and evaporated to give 632 mg of a dark brown semi-solid. Purification of the semi-solid by preparative TLC (5% EtOAc/hexane) lead to separation of the isomers, yielding 6,7- cyclohexeno- 8-phenylquinoline as a light yellow oil (123 mg, 31% yield), and 5,6-cyclohexeno-8-phenylquinoline as a light yellow oil (41 mg 10% yield).

Analytical data for 6,7-cyclohexeno-8-phenyl-quinoline: $^1$H NMR (300 MHz, $CDCl_3$) δ 8.76 (dd, 1H, J=1.8, 4.1), 8.04 (dd, 1H, J= 1.7, 8.2), 7.56 (s, 1H), 7.53-7.24 (m, 6H), 3.06-3.02 (m, 2H), 2.65-2.61 (m, 2H), 1.88-1.71 (m, 4H); $^{13}$C NMR (300 MHz, $CDCl_3$) δ 149.56, 145.83, 139.48, 138.02, 136.96, 135.01, 130.06, 128.23, 126.91, 126.56, 126.12, 120.10, 30.40, 29.00, 23.15, 22.73; MS m/z 259; IR (KBr) $v_{max}$ 2926, 2856, 1599, 1558, 1479, 1442, 1433, 1369, 1250, 1032 cm$^{-1}$; Elem. analysis calcd. for $C_{19}H_{17}N$: C, 87.99; H, 6.61; N, 5.40. Found: C, 88.05; H, 6.25; N, 5.63.

Analytical data for 5,6-cyclohexeno-8-phenyl-quinoline: $^1$H NMR (300 MHz, $CDCl_3$) δ 8.88 (dd, 1H, J=1.8, 4.2), 8.34 (dd, 1H, J= 1.7, 8.5), 7.68-7.65 (m, 2H), 7.51-7.37 (m, 5H), 3.15-3.11 (m, 2H), 2.98-2.94 (m, 2H), 2.05-1.89 (m, 4H); $^{13}$C NMR (300 MHz, $CDCl_3$) δ 148.73, 145.09, 139.84, 138.28, 134.75, 132.62, 131.41, 131.17, 130.54, 127.91, 127.77, 127.08, 120.51, 30.17, 25.22, 22.91, 22.81; HRMS calcd. for $C_{19}H_{17}N$ 258.1283, found 258.1288.

Example 15

Preparation of Compounds of Formula I

A. Formula I where $R^1$ and $R^2$ taken together and $R^2$ and $R^3$ taken together represent —$CH_2$—$CH_2$—$CH_2$—$CH_2$—, and $R^4$ is 3-Chlorophenyl A mixture of 8-bromo- 6,7-cyclohexenoquinoline and 8-bromo-5,6-cyclohexenoquinoline at a ratio of 5 to 1 (1.0 g, 3.8 mmol), prepared for example as shown in Example 14, was combined with (1.2 g, 7.6 mmol), palladium tetrakis triphenylphosphine (0.17 g, 0.15 retool) and 2M aqueous $Na_2CO_3$ solution (7.6 ml, 15.2 mmol) in 20 ml of ethanol/benzene (1:1 vol). The reaction mixture was refluxed for 20 hours, then the solvents evaporated, and the residue dissolved in EtOAc and washed with $H_2O$. The aqueous layer was extracted with EtOAc and the combined organic layers were washed with $H_2O$, brine, dried over $Na_2SO_4$, filtered and evaporated. Purification by flash column chromatography (5% acetone/hexane) yielded 8-(3'-chlorophenyl)-6,7-cyclohexenoquinoline (370 mg, 33.0% yield) as a white solid and 8-(3'-chlorophenyl)-5,6-cyclohexenoquinoline (177 mg, 15.8% yield) as a light yellow oil.

Analytical data for 8-(3'-chlorophenyl)-6,7-cyclohexenoquinoline: m.p. 118°–120 ° C., 1H NMR (300 MHz, $CDCl_3$) δ 8.77 (dd, 1H, J=1.8, 4.2), 8.04 (dd, 1H, J=1.8, 8.3), 7.57 (s, 1H0, 7.45-7.35 (m, 2H), 7.27 (s, 1H), 7.26 (dd, 1H, J=4.2, 8.2), 7.18-7.15 (m, 1H), 3.06-3.02 (m, 2H0, 2.71-2.53 (m, 2H0, 1.88-1.75 (m, 4H); $^{13}$C NMR (300 MHz, $CDCl_3$) δ 149.66, 145.58, 141.19, 138.04, 138.00, 136.98, 135.06, 134.05, 130.27, 129.47, 128.47, 127.15, 126.56, 30.35, 28.96, 23.08, 22.66; MS m/z 293; IR (KBr) $v_{max}$ 2953, 2934, 1593, 1560, 1485, 1471, 1446, 1435, 1367, 1163, 1076 cm$^{-1}$; Elem. analysis calcd. for $C_{19}H_{16}ClN$: C, 77.68; H, 5.49; N, 4.77. Found: C, 77.75; H, 5.39; N, 4.87.

Analytical data for 8-(3'-chlorophenyl)-5,6-cyclohexenoquinoline: $^1$H NMR (300 MHz, $CDCl_3$) δ 8.87 (dd, 1H, J= 1.7, 4.1), 8.33 (dd, 1H, J=1.8, 8.6), 7.66-7.65 (m, 1H), 7.51-7.54 (m, 1H), 7.42 (s, 1H), 7.41-7.32 (m, 4H), 3.13-3.09 (m, 2H), 2.96-2.92 (m, 2H), 2.02-1.86 (m, 4H); $^{13}$C NMR (300 MHz, $CDCl_3$) δ 148.89, 144.85, 141.65, 136.80, 134.78, 133.70, 132.61, 132.11, 131.26, 130.56, 129.06, 128.88, 127.78, 127.13, 120.70, 30.16, 25.24, 22.85, 22.77; HRMS calcd. for $C_{19}H_{16}NCl$: 292.0893, found: 292. 0897.

Example 16

Preparation of Compounds of Formula I

A. Formula I where $R^1$ and $R^2$ taken together and $R^2$ and $R^3$ taken together represent —$CH_2$—$CH_2$—$CH_2$—$CH_2$— and $R^4$ is 3-Nitrophenyl A mixture of 8-bromo- 6,7- cyclohexenoquinoline and 8-bromo-5,6-cyclohexenoquinoline at a ratio of 5 to 1 (5.7 g, 21.7 mmol), prepared for example as shown in Example 15, was combined with 3-nitrobenzeneboronic acid (7.3 g, 43.5 mmol), palladium tetrakis triphenylphosphine (1.00 g, 0.86 mmol) and 2M aqueous $Na_2CO_3$ solution (43.5 ml, 87.0 mmol) in 100 ml of ethanol/benzene (1:1 vol). The reaction mixture was refluxed for 4.5 hours, the solvents evaporated, and the residue dissolved in EtOAc and washed with $H_2O$. The aqueous layer was extracted with EtOAc and the combined organic layers were washed with $H_2O$, brine, dried over $Na_2SO_4$, filtered and evaporated, yielding 11.6 g of crude solid material. Purification by flash column chromatography (10% EtOAc/hexane) yielded 5,6-cyclohexeno-8-(3'-nitrophenyl)quinoline (1.1 g, 16.7% yield) as a pure white solid, and 6,7-cyclohexeno-8-(3'-nitrophenyl)quinoline as a slightly impure, light yellow solid (5.3 g), which was recrystallized from acetone, followed by trituration of the recovered crystals with ether, yielding 6,7-cyclohexeno-8-(3'-nitrophenyl) quinoline (3.5 g, 54.0% yield) as a white solid.

Analytical data for 6,7-cyclohexeno-8-(3'-nitrophenyl)quinoline: m.p. 151°–152 ° C.; $^1$H NMR (300 MHz, $CDCl_3$) δ 8.73 (dd, 1H, J=1.8, 4.2), 8.27 (dr, 1H, J=2.4, 6.8), 8.19 (t, 1H, J=2.8), 8.08 (dd, 1H, J=1.8, 8.3), 7.67 (s, 1H), 7.65-7.63 (m, 1H), 7.30 (dd, 1H, J=4.2, 8.3), 3.08-3.04 (m, 2H0, 2.71-2.53 (m, 2H), 1.90-1.73 (m, 4H); $^{13}$C NMR (300 MHz, $CDCl_3$) δ 149.71, 148.29, 145.36, 140.99, 138.06, 137.13, 136.83, 135.23, 129.05, 127.11, 126.62, 125.49, 122.11, 120.51, 30.28, 29.07, 23.00, 22.57; MS m/z 304; IR (IBr) $v_{max}$ 2937, 2866, 1593, 1560, 1525, 1487, 1450, 1429, 1346, 1302, 1076 cm$^{-1}$; Elem. analysis calcd. for $C_{19}H_{16}N_2O_2$: C, 74.98; H, 5.30, N, 9.20. Found: C, 75.17; H, 5.30; N, 9.37.

Analytical data for 5,6-cyclohexeno-8-(3'-nitrophenyl)quinoline: m.p. 172°–174° C.; $^1$H NMR (300 MHz, $CDCl_3$) δ 8.87 (dd, 1H, J=1.7, 4.3), 8.57 (t, 1H, J=2.0), 8.38 (dd, 1H, J=1.7, 8.7), 8.24 (ddd, 1H, J-1.1, 2.3, 8.2), 8.04 (ddd, 1H, J=1.1, 2.2, 8.2), 7.63 (t, 1H, J=2.0), 7.45 (dd, 1H, J=4.1, 8.7), 3.17-3.13 (m, 2H), 3.00-2.96 (m, 2H), 2.05-1.89 (m, 4H). $^{13}$C NMR (300 MHz, $CDCl_3$) δ 149.07, 148.09, 144.56, 141.42, 136.94, 135.60, 135.01, 132.97, 132.79, 131.52, 128.68, 127.91, 125.57, 122.00; MS m/z 304; IR (KBr) $v_{max}$ 2953, 2936, 2928, 2860, 1589, 1574, 1525, 1498, 1481, 1456, 1435, 1369, 1344, 1298, 1093 cm$^{-1}$; Elem. analysis calcd. for $C_{19}H_{16}N_2O_2$: C, 74.98; H, 5.30; N, 9.20. Found: C, 74.82; H, 5.18; N, 9.42.

Example 17

Preparation of Compounds of Formula I

A. Formula I where $R^1$ and $R^2$ taken together and $R^2$ and $R^3$ taken together represent —CH$_2$—CH$_2$—CH$_2$—CH$_2$—, varying $R^4$ By following the procedures described in Examples 14, 15 and 16 (immediately preceding) and substituting the various boronic acids (i.e. compounds of Formula 4) with other compounds of Formula 4, there are obtained the following representative compounds of Formula I where $R^1$ and $R^2$ taken together and $R^2$ and $R^3$ taken together represent —CH$_2$—CH$_2$—CH$_2$—CH$_2$—.
8-(3'-chloro-4'-fluorophenyl)-6,7-cyclohexenoquinoline;
8-(4'-chlorophenyl)-6,7-cyclohexenoquinoline;
6,7-cyclohexeno-8-(3', 4'-dichlorophenyl)quinoline;
8-(3'-bromophenyl)-6,7-cyclohexenoquinoline;
6,7-cyclohexeno-8-(3'-trifluoromethylphenyl)quinoline;
6,7-cyclohexeno-8-(4'-trifluoromethylphenyl)quinoline;
8-(4'-bromophenyl)-6,7-cyclohexenoquinoline;
8-(3'-chloro-4'-fluorophenyl)-5,6-cyclohexenoquinoline;
8-(4'-chlorophenyl)-5,6-cyclohexenoquinoline;
5,6-cyclohexeno-8-(3', 4'-dichlorophenyl)quinoline;
8-(3'-bromophenyl)-5,6-cyclohexenoquinoline;
5,6-cyclohexeno-8-(3'-trifluoromethylphenyl)quinoline;
5,6-cyclohexeno-8-(4'-trifluoromethylphenyl)quinoline; and
8-(4'-bromophenyl)-5,6-cyclohexenoquinoline.

B. Formula I where $R^1$ and $R^2$ taken together and $R^2$ and $R^3$ taken together represent —CH$_2$—CH$_2$—CH$_2$—CH$_2$— and $R^4$ is 3,4-Methylenedioxyphenyl By following the procedures described in Example 5, but substituting 8-bromo-5,6-cyclopentenoquinoline with the mixture of 8-bromo-6,7-cyclohexenoquinoline and 8-bromo-5,6-cyclhexenoquinoline (from Example 15), there are obtained the corresponding substituted compounds of Formula I where $R^2$ and $R^3$ taken together represent —CH$_2$—CH$_2$—CH$_2$—CH$_2$—, i.e. 6,7-cyclohexeno-8-(3,4-methylenedioxyphenyl)quinoline, and $R^1$ and $R^2$ taken together represent —CH:—CH$_2$—CH$_2$—CH$_2$—, i.e. 5,6-cyclohexeno-8-(3,4-methylenedioxyphenyl)quinoline].

Example 18

Preparation of Salts of Compounds of Formula I

Hydrochloride salt of a Formula I where $R^1$ and $R^2$ taken together represent —CH$_2$—CH$_2$—CH$_2$—CH$_2$—, and $R^4$ is 3-Nitrophenyl 6,7-Cyclohexeno-8-(3'-nitrophenyl)quinoline (3.4 g, 11.2 mmol) was dissolved in EtOAc (35 ml). To this solution, EtOAc saturated with HCl was added dropwise, resulting in the formation of a precipitate. The dropwise addition continued until no additional solid precipitate was formed. The white solid was filtered off, washed with acetone (3 x) and dried under reduced pressure to yield the hydrochloride salt, i.e., 6,7-cyclohexeno-8-(3'-nitrophenyl)quinoline hydrochloride (3.4 g, 89% yield) as a white solid.

Analytical data: m.p. 235 ° C. (decomp.); $^1$H NMR (300 MHz, CDCl$_3$) δ 9.26 (dd, 1H, J=1.6, 5.4), 8.86 (dd, 1H, J=1.6; 8.3), 8.47 (ddd, 1H, J=1.2, 2.5, 8.2), 8.20 (t, 1H, J-1.9), 7.99 (s, 1H), 7.91-7.86 (m, 2H), 7.69 (dd, 1H, J=1.2, 2.5, 8.2), 3.19-3.15 (m, 2H), 2.76-2.60 (m, 2H0, 1.96-1.79 (m, 4H); $^{13}$C NMR (300 MHz, CDCl$_3$) δ 149.29, 146.14, 145.48, 145.20, 141.93, 136.54, 135.15, 134.34, 131.69, 127.94, 127.43, 125.55, 124.96, 120.53, 30.37, 29.49, 22.21, 21.80; MS m/z 304 (free base); IR(KBr) $v_{max}$ 2936, 2864, 1628, 1595, 1527, 1431, 1385, 1348, 1300, 1242 cm$^{-1}$; Elem. analysis calcd. for $C_{19}H_{16}N_2O_2$•HCl: C, 66.96; H, 5.03; N, 8.22; Cl, 10.40. Found: C, 66.89; H, 4.93; N, 8.11; Cl, 10.72.

Example 19

Determination of Potency and Selectivity of Inhibitors for PDE IV

Preparation of Human Platelet Phosphodiesterase (PDE III)

Platelet high-affinity cAMP PDE (PDE III) was obtained from human blood in accordance with previously described procedures described in *Mol. Pharmacol.* 20:302–309, Alvarez, R., Taylor, A., Fazarri, J. J., and Jacobs, J. R. (1981).

Blood was collected into evacuated tubes containing EDTA (7.7 mM, final concentration). PRP was obtained by centrifuging the blood in polycarbonate tubes at 200 x g for 15 min at 4° C. A platelet pellet was resuspended in a volume of buffer A (0.137M NaCl, 12.3 mM Tris-HCl buffer, pH 7.7, containing 1 mM MgCl$_2$. The hypotonically-lysed platelet suspension was centrifuged at 48,000 x g for 15 min and the supernatant was saved. The pellets were frozen on dry ice and briefly thawed at 22° C. The supernatant was combined with the pellet fraction and the resulting suspension was centrifuged at 48,000 x g for 30 min. The supernatant fraction was stored in 0.5 mL aliquots at –20° C. and used as the soluble PDE. Enzyme activity was adjusted to 10–20% hydrolysis after 10 minutes of incubation by dilution with 10 mM cold Tris-HCl buffer, pH7.7.

Preparation of Human Lymphocyte Phosphodiesterase (PDE IV)

Human B cell line (43D) were cultured at 37° C. in 7% CO$_2$ in RPMI 1640 with L-glutamine and 10% Nu-Serum. Prior to the assay –1.5×10$^8$ cells were centrifuged at 1000 rpm for 10 minutes in a table top clinical centrifuge. The pellet was resuspended in 2–3 mL of 45 mM Tris-HCl buffer, pH 7.4. The suspension was homogenized and centrifuged at 12,000 x g 4° C. for 10 minutes. The supernatant was diluted to 28 mL with Tris-HCl buffer and used directly in the assay or stored at –20° C. The final concentration of DMSO in the PDE incubation medium was 1%. Nitraquazone was included in each assay (10 and 100 μM) as a reference standard.

Human Platelet cAMP Phosphodiesterase Assay

The phosphodiesterase incubation medium contained 10 mM Tris-HCl buffer, pH 7.7, 10 mM MgSO$_4$, 0.1–1μM [$^3$H]-AMP (0.2 μCi) in a total volume of 1.0 mL. Following addition of the enzyme, the contents were mixed and incubated for 10 min at 30° C. The reaction was terminated by immersing the tubes in a boiling-water bath for 90 sec. After the tubes were cooled in an ice-water bath, 0.1 mL (100 μg) of 5'-nucleotidase from snake venom (Crotalus atrox, Sigma V-7000) was added to each tube. The contents were mixed and incubated for 30 min at 30° C. The nucleotidase reaction was terminated by immersing the tubes in a boiling water bath for 60 sec. Labeled adenosine was isolated from alumina columns according to the method described in *Anal. Biochem.*, 52:505–516 (1973), Filburn, C. R., and Karn, *J. Assays* were performed in triplicate. Hydrolysis of cAMP ranged from 10–20%. Test compounds were dissolved in DMSO. The final concentration of DMSO in the phosphodiesterase assay was 1% when tested with compounds up to 0.1 mM. When tested at 1 mM the DMSO concentration was 10% and this activity was compared to control PDE activity in the presence of 10% DMSO.

Human Lymphocyte cAMP Phosphodiesterase Assay

The phosphodiesterase incubation medium contained 40 mM Tris-HCl buffer, pH 7.7, 0.1 mM $MgSO_4$, 3.75 mM mercaptoethanol, and 0.1–1.0 µM [$^3$H] cAMP (0.2 µCi) in a total volume of 1.0 mL. The reaction was performed and processed according to the procedure used (above) for human platelet PDE. The final concentration of DMSO was 1%.

The compounds of the present invention exhibit potency and selectivity as inhibitors of PDE IV when tested by the human platelet cAMP phosphodiesterase assay and the human lymphocyte cAMP phosphodiesterase assay.

Example 20

Determination of Immunosuppressive Activity

Utilizing Responses of Human Peripheral Blood

Lymphocytes to Mitogen

This procedure is a modification of a procedure initially described by Greaves, et al. ["Activation of human T and B lymphocytes by polyclonal mitogens," *Nature*, 248, 698–701 (1974)].

Human mononuclear cells (PBL) were separated from heparinized whole blood by density gradient centrifugation in Ficoll-Paque (Pharmacia). After washing, $5 \times 10^4$ cells/well are cultured in microtiter plates with minimal essential media supplemented with 1% human serum, gentamicin, sodium bicarbonate, 2-mercaptoethanol, glutamine, non-essential amino acids, and sodium pyruvate. The mitogen concanavalin A (Sigma) is used at a concentration of 2 µg/ml. Test materials are tested at concentrations between $10^{-4}$ and $10^{-10}$M, by addition to the culture at time 0. Cultures are set up in quadruplicate and incubated at 37° C. in a humidified atmosphere with 5% $CO_2$ for 48 hours. A pulse of 1.0 µCi/well of 3H-thymidine is added for the last 4 hours. Cells are collected on glass fiber filters with an automatic harvester and radioactivity is measured by standard scintillation procedures. The 50% inhibitory concentration ("$IC_{50}$") for mitogenic stimulation is determined graphically.

The compounds of the present invention showed immunosuppressive activity when tested by this method.

Example 21

Determination of Immunosuppressive Activity

Utilizing The Hemolytic Plaque Forming Cell Assay

This procedure is a modification of "The agar plaque technique for recognizing antibody producing cells," a procedure initially described by Jerne, et al. [*Cell-bound Antibodies*, Amos and Kaprowski editors (Wistar Institute Press, Philadelphia, 1963) p. 109].

Groups of 5–6 adult C3H female mice were sensitized with $1.25 \times 10^8$ sheep red blood cells (SRBC) and simultaneously treated with an oral dosage form of the test material in an aqueous vehicle. Animals in a control group receive the same volume of vehicle. Four days after SRBC inoculation, spleens are dispersed in glass homogenizers. The number of nucleated cells (WBC) is determined and the spleen cell suspension is mixed with SRBC, guinea pig complement and agar solution at 0.5% concentration. Aliquots of the above mixture (0.1 mL) are dropped on four separate quadrants of a Petri dish and are covered with cover slips. After two hours incubation at 37° C., areas of hemolysis around plaque-forming cells (PFC) are counted with a dissecting microscope. Total WBC/spleen, PFC/spleen and PFC/$10^6$ WBC (PPM) are calculated for each mouse spleen. Geometric means of each treatment group are then compared with the vehicle-treated control group.

The compounds of the present invention showed immunosuppressive activity when tested by this method.

Example 22

Determination of Anti-Inflammatory Activity Utilizing

Arachidonic Acid-Induced Ear Edema in the Mouse

This procedure is a modification of a procedure described by Young et al., *J. Invest. Derm.*, 82:367–371 (1984).

Female Charles River ICR mice 23–27 grams are administered 0.2 mL of test material. The mice are later challenged with 20 µl of arachidonic acid applied topically to the ear. One hour after challenge, the weight of an 8 mm disc is determined. The mean increase in ear plug weight is calculated. Materials with anti-inflammatory activity inhibit the increase in ear plug weight.

The compounds of the present invention exhibited anti-inflammatory activity when tested by this method.

Example 23

Determination of Anti-Inflammatory Activity Utilizing

Adjuvant-Induced Arthritis In The Rat

This procedure is a modification of a procedure initially described by Pearson, C. M., *Proc. Soc. Exp. Biol. Med.*, 91:95–101 (1956).

Female Charles River albino rats weighing 160–180 g receive 0.1 mL of a suspension in paraffin oil of heat-killed *Mycobacterium butyricum* (10 mg/ml) by means of an intradermal injection into the proximal ¼ of the tail on day 0. Beginning on day 1, the test material is administered orally in an aqueous vehicle (0.5 mL/dose) once each day for 17 days. On day 18 the intensity of the swelling of the four foot pads and tail is determined utilizing a scoring system in which the swelling in the four paws was scored 0–4 for each paw and the tail swelling is scored 0–3, such that the total maximum score is 19.

The compounds of the present invention exhibited anti-inflammatory activity when tested by this method.

Example 24

Determination of Activity Towards Autoimmune Disease Utilizing Survival of MRL/1 pr Mice MRL/1 pr mice develop a multisystemic disease characterized by glomerulonephritis, arthritis, arteritis, lymphoid hyperplasia. The length of survival of mice with this disease is approximately one-third that of non-disease developing MRL/n mice. These mice have a high incidence of autoantibodies and the disease process is considered autoimmune in nature as described by Theofilopoulos, et al., *Advances in Immunology*, 37:269–390 (1985).

The compounds of the present invention significantly extended the lifespan of the MRL/lpr mice.

EXAMPLE 25

Determination of Analgetic Activity Utilizing Phenylquinone-Induced Stretching in the Mouse This procedure is a modification of a procedure described by Hendershoot, et al. *J. Pharmacol. Exp. Ther.*, 125:237–240 (1959).

Groups of 8 Female CD-1 mice are administered test materials orally in an aqueous vehicle. At various times following administration of test materials, 0.25 mL of a 0.02% solution of phenylquinone is administered intraperitoneally. The number of stretches for each animal is enumerated over a ten minute period following the phenylquinone administration. Analgetic activity is determined by inhibition of the mean number of stretches.

The compounds of the present invention showed analgetic activity when tested by this method.

EXAMPLE 26

Capsule Formulation

This example illustrates the preparation of a representative pharmaceutical formulation for oral administration containing an active compound of Formula I, e.g. 8-(3-chlorophenyl)-5,6-cyclopentenoquinoline.

| Ingredients | Quantity (mg/capsule) |
| --- | --- |
| Active compound | 200 |
| lactose, spray-dried | 148 |
| magnesium stearate | 2 |

The above ingredients are mixed and introduced into a hard-shell gelatin capsule.

Other compounds of Formula I, such as those prepared in accordance with Examples 1–18 can be used as the active compound in the preparation of the orally administrable formulations of this example.

EXAMPLE 27

Oral Formulation

This example illustrates the preparation of a representative pharmaceutical formulation containing an active compound of Formula I, e.g., 6,7-cyclopenteno-8-(3-nitrophenyl)quinoline.

An suspension for oral administration is prepared having the following composition:

| Ingredients | Quantity |
| --- | --- |
| Active compound | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Other compounds of Formula I, such as those prepared in accordance with Examples 1–18 can be used as the active compound in the preparation of the orally administrable formulations of this example.

Example 28

Tablet Formulation

This example illustrates the preparation of a representative pharmaceutical formulation containing an active compound of Formula I, e.g. 8-(3-chlorophenyl)-5,6-cyclohexenoquinoline.

A tablet for oral administration is prepared having the following composition:

| Ingredients | Quantity (mg/capsule) |
| --- | --- |
| Active compound | 400 |
| corn starch | 50 |
| lactose | 145 |
| magnesium stearate | 5 |

The above ingredients are mixed intimately and pressed into single scored tablets.

Other compounds of Formula I, such as those prepared in accordance with Examples 1–18 can be used as the active compound in the preparation of the tablet formulations of this example.

Example 29

Injectable Formulation

This example illustrates the preparation of a representative pharmaceutical formulation containing an active compound of Formula I, e.g., 6,7-cyclohexeno-8-(3-nitrophenyl)quinoline.

An injectable preparation is prepared having the following composition:

| Ingredients | Quantity |
| --- | --- |
| Active compound | 0.2 g |
| water (distilled, sterile) | q.s. to 20.0 mL |

Other compounds of Formula I, such as those prepared in accordance with Examples 1–18 can be used as the active compound in the preparation of the injection administrable formulations of this example.

Example 30

Suppository Formulation

This example illustrates the preparation of a representative pharmaceutical formulation containing an active compound of Formula I, e.g., 8-(3-chlorophenyl)-5,6-cyclopentenoquinoline.

A suppository totalling 2.5 grams is prepared having the following composition:

| Ingredients | Quantity |
|---|---|
| Active compound | 500 mg |
| witepsol H-15* | q.s. to 2.5 g |

(*triglycerides of saturated vegetable fatty acid; a product of Riches-Nelson, Inc., New York, N.Y.).

Other compounds of Formula I, such as those prepared in accordance with Examples 1–18 can be used as the active compound in the preparation of the suppository formulations of this example.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound represented by the formula

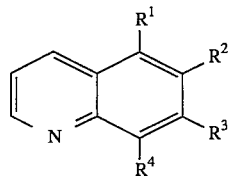

wherein:

$R^1$ and $R^2$ taken together represent —$CH_2$—$CH_2$—$CH_2$— or —$CH_2$—$CH_2$—$CH_2$—$CH_2$— and $R^3$ is hydrogen; or $R^2$ and $R^3$ taken together represent —$CH_2$—$CH_2$—$CH_2$— or —$CH_2$—$CH_2$—$CH_2$—$CH_2$— and $R^1$ is hydrogen; and $R^4$ is phenyl optionally mono-, di-, or tri-substituted independently with lower alkyl, lower alkoxy, hydroxy, nitro, trifluoromethyl, halo, thiol, amino, nitro, lower alkylthio, mono-lower-alkylamino, di-lower alkylamino, hydroxycarbonyl, lower alkoxycarbonyl, methylcarbonyl, hydroxysulfonyl, lower alkoxysulfonyl, lower alkylsulfonyl, lower alkylsulfinyl, cyano, tetrazoyl, carbamoyl, lower alkylcarbamoyl, di-lower alkylcarbamoyl and methylenedioxy;

provided that no more than one methylenedioxy substituent, no more than two nitro or no more than two iodo substituents are present, or a pharmaceutically acceptable salt or N-oxide thereof.

2. The compound of claim 1 wherein $R^4$ is phenyl optionally mono-substituted by methylenedioxy, or phenyl optionally mono-, or disubstituted by lower alkyl, lower alkoxy, hydroxycarbonyl, methoxy carbonyl, methylcarbonyl, halo, nitro, trifluoromethyl, cyano, or carbamoyl, or a pharmaceutically acceptable salt or N-oxide thereof.

3. The compound of claim 2 wherein $R^1$ and $R^2$ taken together represent —$CH_2$—$CH_2$—$CH_2$—$CH_2$—, or a pharmaceutically acceptable salt or N-oxide thereof.

4. The compound of claim 3 wherein $R^4$ is phenyl, or a pharmaceutically acceptable salt or N-oxide thereof.

5. The compound of claim 3 wherein $R^4$ is 3-nitrophenyl, or a pharmaceutically acceptable salt or N-oxide thereof.

6. The compound of claim 3 wherein $R^4$ is 3-chlorophenyl, or a pharmaceutically acceptable salt or N-oxide thereof.

7. The compound of claim 2 wherein $R^1$ and $R^2$ are —$CH_2$—$CH_2$—$CH_2$—, or a pharmaceutically acceptable salt or N-oxide thereof.

8. The compound of claim 7 wherein $R^4$ is phenyl, or a pharmaceutically acceptable salt or N-oxide thereof.

9. The compound of claim 7 wherein $R^4$ is 3-nitrophenyl, or a pharmaceutically acceptable salt or N-oxide thereof.

10. The compound of claim 7 wherein $R^4$ is 3,4-methylenedioxyphenyl, or a pharmaceutically acceptable salt or N-oxide thereof.

11. The compound of claim 7 wherein $R^4$ is 3-chloro-4-fluorophenyl, 3-chlorophenyl, 4-chlorophenyl, or 3-fluorophenyl, or a pharmaceutically acceptable salt or N-oxide thereof.

12. The compound of claim 2 wherein $R^2$ and $R^3$ taken together represent —$CH_2$—$CH_2$—$CH_2$—$CH_2$—, or a pharmaceutically acceptable salt or N-oxide thereof.

13. The compound of claim 12 wherein $R^4$ is phenyl, or a pharmaceutically acceptable salt or N-oxide thereof.

14. The compound of claim 12 wherein $R^4$ is 3-nitrophenyl, or a pharmaceutically acceptable salt or N-oxide thereof.

15. The compound of claim 12 wherein $R^4$ is 3-chlorophenyl, or a pharmaceutically acceptable salt or N-oxide thereof.

16. The compound of claim 2 wherein $R^2$ and $R^3$ are —$CH_2$—$CH_2$—$CH_2$—, or a pharmaceutically acceptable salt or N-oxide thereof.

17. The compound of claim 16 wherein $R^4$ is phenyl, or a pharmaceutically acceptable salt or N-oxide thereof.

18. The compound of claim 16 wherein $R^4$ is 3-nitrophenyl, or a pharmaceutically acceptable salt or N-oxide thereof.

19. The compound of claim 16 wherein $R^4$ is 3-chlorophenyl, or a pharmaceutically acceptable salt or N-oxide thereof.

20. A pharmaceutical composition comprising a pharmaceutically acceptable non-toxic excipient and a therapeutically effective amount of a compound of claim 1, or a pharmaceutically acceptable salt or N-oxide thereof.

21. A method of use of a compound of claim 1, or a pharmaceutically acceptable salt or N-oxide thereof, as an anti-inflammatory agent anti-allergic agent, anti-asthma agent, anti=rhinitis agent, bronchodilation agent, or analgetic agent, by administering to a mammal in need of such treatment a therapeutically effective amount for each of the above uses of a compound of claim 1, or a pharamceutically acceptable salt or N-oxide thereof, to a mammal in need thereof.

* * * * *